US010221397B2

(12) United States Patent
Wang et al.

(10) Patent No.: US 10,221,397 B2
(45) Date of Patent: *Mar. 5, 2019

(54) PROTEIN-INDUCED PLURIPOTENT CELL TECHNOLOGY AND USES THEREOF

(71) Applicant: Wayne State University, Detroit, MI (US)

(72) Inventors: Jianjun Wang, Troy, MI (US); Qianqian Li, Troy, MI (US)

(73) Assignee: Wayne State University, Detroit, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/808,205

(22) Filed: Nov. 9, 2017

(65) Prior Publication Data

US 2018/0127725 A1 May 10, 2018

Related U.S. Application Data

(62) Division of application No. 14/113,522, filed as application No. PCT/US2012/036051 on May 2, 2012, now Pat. No. 9,816,076.

(60) Provisional application No. 61/481,273, filed on May 2, 2011.

(51) Int. Cl.
*C12N 5/074* (2010.01)

(52) U.S. Cl.
CPC ...... *C12N 5/0696* (2013.01); *C12N 2501/115* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2506/1307* (2013.01)

(58) Field of Classification Search
CPC ............ C12N 5/0696; C12N 2501/115; C12N 2501/602; C12N 2501/603; C12N 2501/604; C12N 2501/605; C12N 2501/606; C12N 2506/1307
See application file for complete search history.

(56) References Cited

U.S. PATENT DOCUMENTS

| 4,666,828 | A | 5/1987 | Gusella |
| 4,801,531 | A | 1/1989 | Frossard |
| 5,192,659 | A | 3/1993 | Simons |
| 5,272,057 | A | 12/1993 | Smulson et al. |
| 8,722,348 | B2 | 5/2014 | Wang et al. |
| 2003/0134352 | A1 | 7/2003 | Freimuth et al. |
| 2004/0185528 | A1 | 9/2004 | Horn et al. |
| 2005/0064545 | A1 | 3/2005 | DeMarco et al. |
| 2005/0074840 | A1 | 4/2005 | Brondyk et al. |
| 2010/0233804 | A1 | 9/2010 | Zhou et al. |

FOREIGN PATENT DOCUMENTS

| WO | WO-2005/026196 | 3/2005 |
| WO | WO-2009/155026 | 12/2009 |
| WO | WO-2010115052 | 10/2010 |
| WO | WO-2010124143 | 10/2010 |
| WO | WO-2010130446 | 11/2010 |
| WO | WO-2011058064 | 5/2011 |

OTHER PUBLICATIONS

Wang Declaration, filed Feb. 2, 2014, in U.S. Appl. No. 14/113,522, pp. 1-4.*
Jaenisch et al., Cell, 132: 567-582, 2008.*
Zangrossi et al., Stem Cells, 25: 1675-1680, 2007.*
Gerecht-Nir, Developmental Dynamics, 232: 487-497 (2005).*
Rostovskaya et al., Phil. Trans. R. Soc. B, 370: 1-11, 2015.*
Amabile, G. et al., Induced pluripotent stem cells: current progress and potential for regenerative medicine, Trends Mol Med. 15:59-68, 2009.
Amit, M., et al., Feeder layer- and serum-free culture of human embryonic stem cells, Biol Reprod, 70(3):837-45, Mar. 2004.
Aridor, M. et al., Traffic Jam: A Compendium of Human Diseases that Affect Intracellular Transport Processes, Traffic, Toolbox 1:836-851, 2000.
Burz, D. et al., Mapping Structural Interactions Using In-Cell NMR Spectroscopy (STINT-NMR), http://www.nature.com/naturemethods, 2006.
Carey, B. et al., Reprogramming of murine and human somatic cells using a single polycistronic vector, Proc Natl Acad Sci USA, 106(1):157-62, Jan. 6, 2009.
Cai et al., An efficient and cost-effective isotope labeling protocol for proteins expressed in *Escherichia coli*, J of Biomolecular NMR, 11:97-102, 1998.
Chan, E. et al., Live cell imaging distinguishes bona fide human iPS cells from partially reprogrammed cells, Nat Biotechnol, 27(11): 1033-7, 2009.
Chang et al., Cellular internalization of fluorescent proteins via arginine-rich intracellular delivery peptide in plant cells, Plant Cell Physiol, 46(3):482-488, 2005.
Cho, H. et al., Induction of pluripotent stem cells from adult somatic cells by protein-based reprogramming without genetic manipulation, Blood, 116, 386-95, 2010.
Dobson, C., Protein Folding and Misfolding, University of Cambridge, 2003.
Feng, B. et al., Reprogramming of fibroblasts into induced pluripotent stem cells with orphan nuclear receptor Esrrb, Nat Cell Biol, 11(2):197-203, 2009.
Futami et al., Intracellular delivery of proteins into mammalian living cells by polyethyenimine-cationization, J of Biosci. & Bioeng., 99(2):95-103, 2005.

(Continued)

*Primary Examiner* — Thaian N Ton
(74) *Attorney, Agent, or Firm* — Dinsmore & Shohl LLP

(57) ABSTRACT

A method of generating protein-induced pluripotent stem cells by delivering bacterial!y expressed reprogramming proteins into nuclei of starting somatic cells using the QQ-protein transduction technique, repeating several cell reprogramming cycles for creating reprogrammed protein-induced pluripotent stem cells, moving the reprogrammed cells into a feeder-free medium for expansion, and expanding and passaging the reprogrammed cells in a whole dish for generating homogeneous piPS cells. Also provided are the piPCS cells formed using this method and uses thereof.

4 Claims, 19 Drawing Sheets

(56) References Cited

OTHER PUBLICATIONS

Gore, A. et al. Somatic coding mutations in human induced pluripotent stem cells. Nature, 471: 63-7, 2011.
Guignet et al., Reversible site-selective labeling of membrane protein in live cells, Nature Biotechnology, 22(4):440-444, 2004.
Hanna, J. et al., Direct cell reprogramming is a stochastic process amenable to acceleration, Nature, 462:595-601, 2009.
Heng, H. et al., Stochastic cancer progression driven by non-clonal chromosome aberrations, J Cell Physiol, 208: 461-72, 2006.
Heng, H. et al., High-resolution mapping of mammalian genes by in situ hybridization to free chromatin, Proc Natl Acad Sci USA, 89: 9509-13, 1992.
Hussein, S. et al., Genome-wide characterization of the routes to pluripotency, Nature, 516(7530):198-206, Dec. 11, 2014.
Jaenisch, R. et al., Stem cells, the molecular circuitry of pluripotency and nuclear reprogramming, Cell, 132: 567-82, 2008.
Kabouridis, P. et al., Biological applications of protein transduction technology, *Trends Biotechnol*, 21:498-503, 2003.
Kaji, K. et al., Virus-free induction of pluripotency and subsequent excision of reprogramming factors, Nature, 458: 771-775, 2009.
Kim, K. et al., Epigenetic memory in induced pluripotent stem cells, Nature, 467: 285-90, 2010.
Kim, J. et al., Pluripotent stem cells induced from adult neural stem cells by reprogramming with two factors, Nature, 454:646-50, 2008.
Kim, D. et al., Generation of human induced pluripotent stem cells by direct delivery of reprogramming proteins, Cell Stem Cell, 4(6):472-6, 2009.
Kiskinis, E. et al., Progress toward the clinical application of patient-specific pluripotent stem cells, J Clin Invest, 120:51-9, 2010.
Knoepfler, P. et al., Deconstructing stem cell tumorigenicity: a roadmap to safe regenerative medicine, Stem Cells, 27(5):1050-6, 2009.
Kumagai et al., Absorptive-mediated endocytosis of cationized albumin and a beta-endorphin-cationized albumin chimeric peptide by isolated brain capillaries, JBC, 262(31):15214-15219, 1987.
Lang, J. et al., Reprogramming cancer cells: back to the future, Oncogene, 32(18):2247-8, May 2, 2013.
Lerou, P., et al., Therapeutic potential of embryonic stem cells, Blood Rev., 19(6):321-31, Nov. 2005.
Li, Q. et al., Real Time Investigation of Protein Folding, Structure, and Dynamics in Living Cells, A invited review in Method in Cell Biology, 90:287-325, 2008.
Lim, J. et al., Partial somatic to stem cell transformations induced by cell-permeable reprogramming factors, Sci Rep, 4:4361, Mar. 12, 2010.
Lin, S. et al., Mir-302 reprograms human skin cancer cells into a pluripotent ES-cell-like state, RNA, 14:2115-24, 2008.
Lister, R. et al., Hotspots of aberrant epigenomic reprogramming in human induced pluripotent stem cells, Nature, 471: 68-73, 2011.
Mahalingam, D. et al., Reversal of aberrant cancer methylome and transcriptome upon direct reprogramming of lung cancer cells, Sci Rep, 2:592, 2012.
Maherali, N. et al., Directly Reprogrammed Fibroblasts Show Global Epigenetic Remodeling and Widespread Tissue Contribution, Cell Stem Cell, 1:55-70, 2007.
Nakagawa, M. et al., Generation of induced pluripotent stem cells without Myc from mouse and human fibroblasts, Nat. Biotechnol, 26: 101-106, 2008.
Nemes, C. et al., Generation of mouse induced pluripotent stem cells by protein transduction, Tissue Eng Part C Methods, 20(5):383-92, May 2014.
Niwa, H. et al., Quantitative expression of Oct-3/4 defines differentiation, dedifferentiation or self-renewal of ES cells, *Nat Genet*, 24(4): 372-6, 2000.
Okita, K. et al., Generation of germline-competent induced pluripotent stem cells, *Nature*, 448:313-7, 2007.
Okita, K. et al., Generation of mouse induced pluripotent stem cells without viral vectors, Science, 322: 949-953, 2008.
Pan, C. et al., Reprogramming human fibroblasts using HIV-1 TAT recombinant proteins OCT4, SOX2, KLF4 and c-MYC, Mol Biol Rep, 37(4):2117-24, Apr. 2010.
Park, I. et al., Reprogramming of human somatic cells to pluripotency with defined factors, Nature, 451:141-146, 2008.
Polo, J. et al., Cell type of origin influences the molecular and functional properties of mouse induced pluripotent stem cells, Nat Biotechnol, 28: 848-55, 2010.
Prochiantz, A., For Protein Transduction, Chemistry Can Win Over Biology, Nature Methods, 4(2): 119-120, 2007.
Raff, M. et al., Two types of astrocytes in cultures of developing rat white matter: differences in morphology, surface gangliosides, and growth characteristics, J Neurosci, 3:1289-1300, 1983.
Robbins, R. et al., Inducible pluripotent stem cells: not quite ready for prime time?, Curr Opin Organ Transplant., 15:61-7, 2010.
Rodin, S. et al., Long-term self-renewal of human pluripotent stem cells on human recombinant laminin-511, Nat Biotechnol, 28: 611-5, 2010.
Rolletschek, A. et al., Induced human pluripotent stem cells: promises and open questions, Biol Chem., 390:845-9, 2009.
Scheper, W. et al., The molecular mechanism of induced pluripotency: a two-stage switch, Stem Cell Rev, 5:204-23, 2009.
Shao, L. et al., Generation of iPS cells using defined factors linked via the self-cleaving 2A sequences in a single open reading frame, Cell Res, 19(3):296-306, Mar. 2009.
Sivashanmugam, A. et al., Practical protocols for production of a very high-yield of recombinant proteins in *Eschericia coli, Protein Science*, 18:936-948, 2009.
Soldner, F. et al., Parkinson's disease patient-derived induced pluripotent stem cells free of viral reprogramming factors, *Cell*,136: 964-977, 2009.
Stadtfeld, M. et al., Induced pluripotent stem cells generated without viral integration, Science, 322: 945-949, 2008.
Takahashi, K. et al., Induction of pluripotent stem cells from adult human fibroblasts by defined factors, Cell, 131: 861-872, 2007.
Takahashi K. et al., Induction of pluripotent stem cells from mouse embryonic and adult fibroblast cultures by defined factors, Cell, 126: 663-76, 2006.
Takahashi, K. et al., Induction of pluripotent stem cells from fibroblast cultures, Nat Protoc. 2(12):3081-9, 2007.
Testoni, N. et al., A New Method of "In-Cell Reverse Transcriptase-Polymerase Chain Reaction" for the Detection of BCR/ABL Transcript in Chronic Myeloid Leukemia Patients, Blood, 87(9), 3822-27, 1996.
Tonge, P. et al., Divergent reprogramming routes lead to alternative stem-cell states, Nature, 516(7530):192-7, Dec. 11, 2014.
Trehin, R. et al., Chances and pitfalls of cell penetrating peptides for cellular drug delivery, *Eur J Pharm Biopharm*, 58:209-23, 2004.
Wang et al., Arginine-rich intracellular delivery peptides noncovalently transport protein into living cells, BBRC, 346:758-767, 2006.
Warren, et al., Highly Efficient Reprogramming to Pluripotency and Directed Differentiation of Human Cells with Synthetic Modified mRNA, Cell Stem Cell, 7: 1-13, 2011.
Werning, M. et al., In vitro reprogramming of fibroblasts into a pluripotent ES-cell-like state, Nature, 448: 318-324, 2007.
Woltjen, K. et al., piggyBac transposition reprograms fibroblasts to induced pluripotent stem cells, Nature, 458: 766-770, 2009.
Wu, J. et al., Stem cells: A designer's guide to pluripotency, Nature, 516(7530):172-3, Dec. 11, 2014.
Yu, J. et al., Human induced pluripotent stem cells free of vector and transgene sequences, Science, 324: 797-801, 2009.
Yu, J. et al., Induced pluripotent stem cell lines derived from human somatic cells, Science, 318: 1917-1920, 2007.
Zhang, X. et al., Terminal differentiation and loss of tumorigenicity of human cancers via pluripotency-based reprogramming, Oncogene, 32(18):2249-60, 2260.e1-21, May 2, 2013.
Zhou, H. et al., Generation of induced pluripotent stem cells using recombinant proteins, Cell Stem Cell, 4(5):381-4, 2009.
Park, I. et al., Disease-specific induced pluripotent stem (IPS) cells, *Cell*, 134(5): 877-86, Sep. 5, 2008.
Ebert, A. et al., Induced pluripotent stem cells from a spinal muscular atrophy patient, *Nature*, 457(7227): 277-80, Jan. 15, 2009.

(56) References Cited

OTHER PUBLICATIONS

Dimos, J. et al., Induced pluripotent stem cells generated from patients with ALS can be differentiated into motor neurons, Science, American Association for the Advancement of Science, 321(5893): 1218-1221, Aug. 29, 2008.

Huangfu, D. et al., Induction of pluripotent stem cells from primary human fibroblasts with only Oc4 and Sox2, Nature Biotechnology, 26(11): 1269-75, Nov. 1, 2008.

Kim, J. et al., Direct reprogramming of human neural stem cells by OCT4, Nature, 461(7264): 649-54, Oct. 1, 2009.

O'Connor, C., Generation and characterization of the protein-induced pluripotent stem (piPS) cells, M.S. Thesis of Graduate School of Wayne State University, Detroit, MI, 2012.

Lai, Y. et al., SRY (sex determining region Y)-box2 (Sox2)/poly ADP-ribose polymerase 1 (Parp1) complexes regulate pluripotency, PNAS, 109(19): 3772-77, Mar. 6, 2012.

Reijo-Pera, R. et al., Gene expression profiles of human inner cell mass cells and embryonic stem cells, Differentiation, 78: 18-23, 2009.

Reubinoff, B. et al., Embryonic stem cell lines from human blastocysts: somatic differentiation in vitro, Nature Biotechnology, 18: 399-404, Apr. 2000.

Thomson, J. et al., Embryonic Stem Cell Lines Derived from Human Blastocysts, Science, 282: 1145-47, Nov. 6, 1998.

UK House of Parliaments' Select Committee on Science and Technology, Fifth Report of Session 2006-07, vol. II, pp. 76-77, Apr. 5, 2007.

Welcsh, P. et al., BRCA1 and BRCA2 and the genetics of breast and ovarian cancer, *Human Molecular Genetics*, 10(7): 705-713, 2001.

Chavez, K. et al., Triple Negative Breast Cancer Cell Lines: One Tool in the Search for Better Treatment of Triple Negative Breast Cancer, *Breast Dis.*, 32(1-2): 35-48, 2010.

Dominiguez-Bendala, J. et al., Islet Cell Therapy and Pancreatic Stem Cells, Handbook of Stem Cells, Chapter 70: Islet Cell Therapy and Pancreatic Stem Cells, pp. 835-853, 2013.

Hochedlinger, K. et al., Ectopic expression of Oct-4 blocks progenitor-cell differentiation and causes dysplasia in epithelial tissues. Cell, 121: 465-477, May 6, 2005.

\* cited by examiner

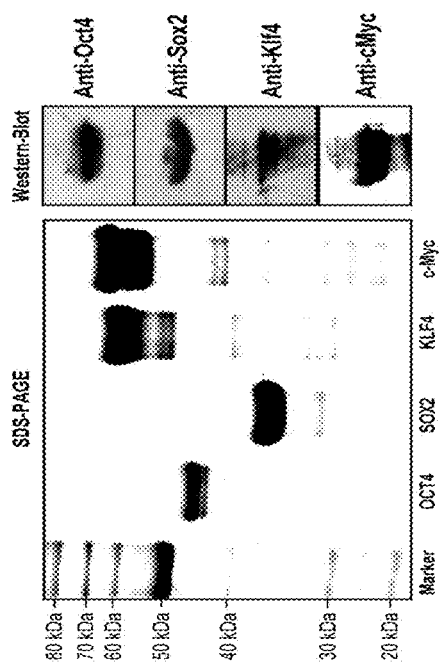
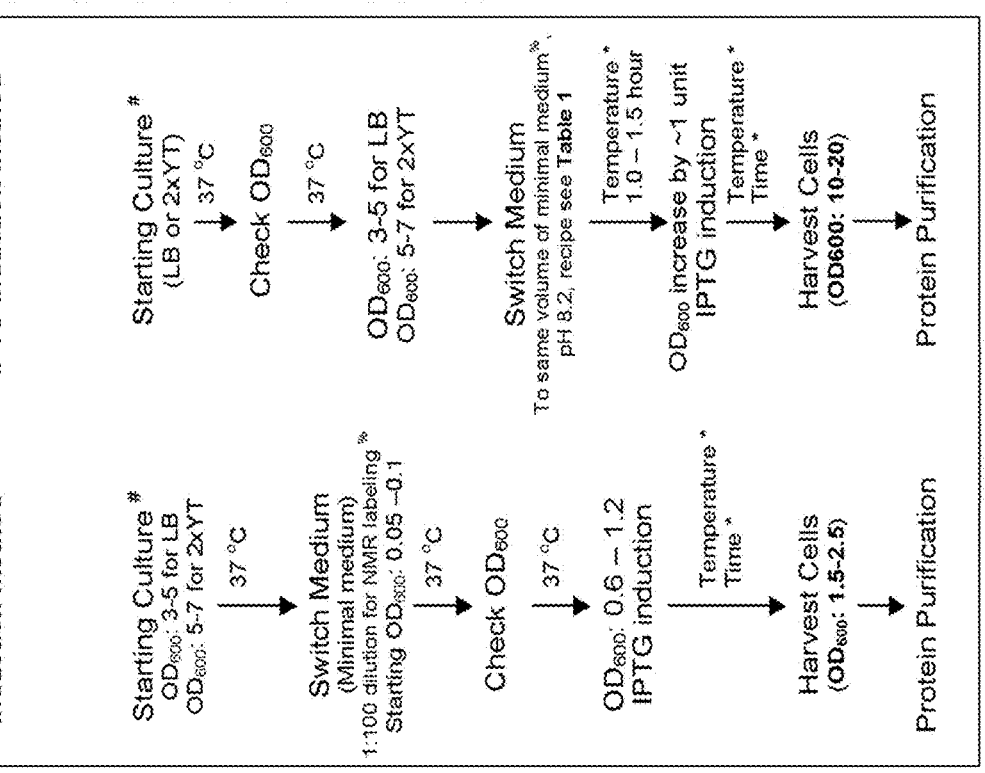
FIG. 2A
FIG. 2B

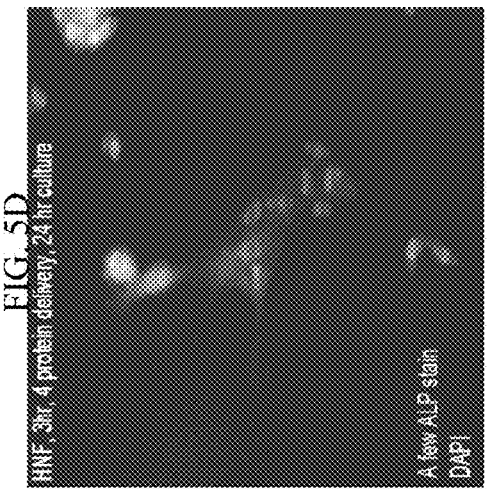
FIG. 5C
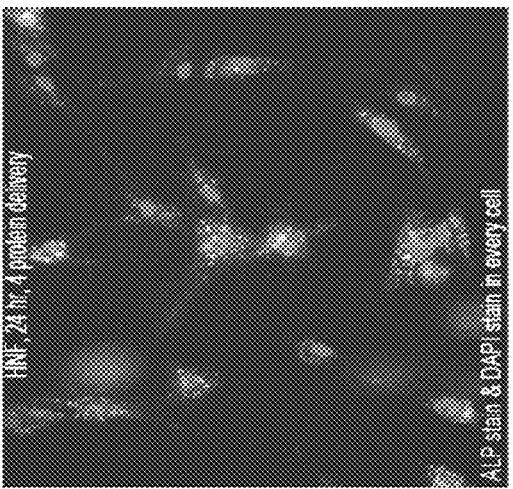
FIG. 5D
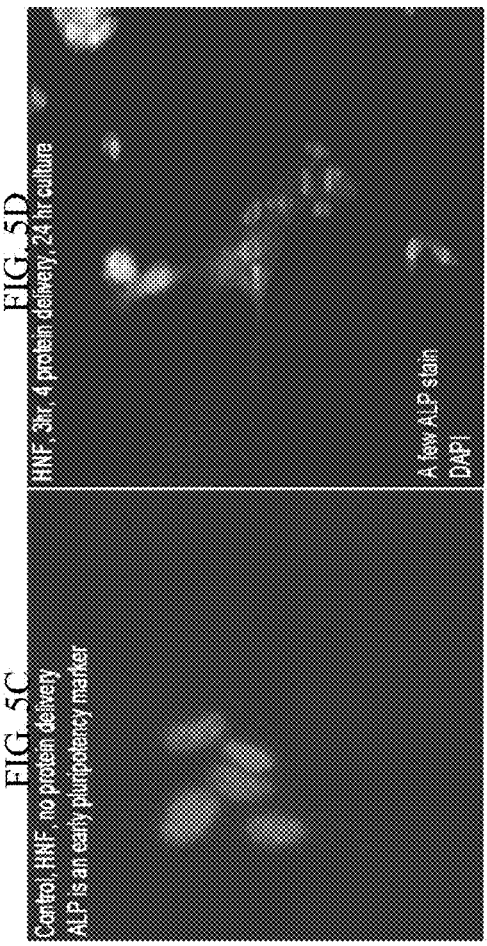
FIG. 5E
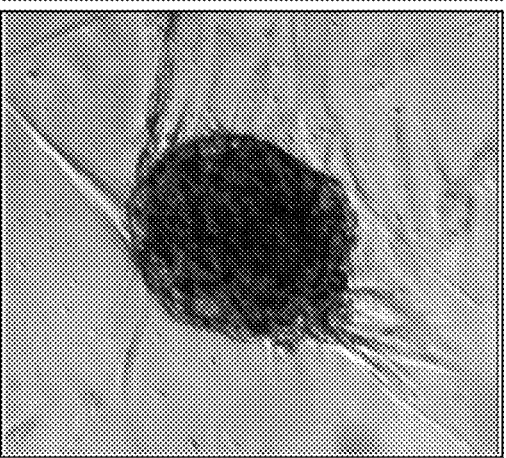
FIG. 5F
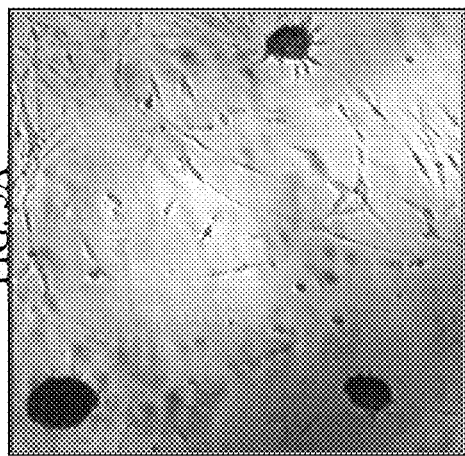
FIG. 5A
FIG. 5B

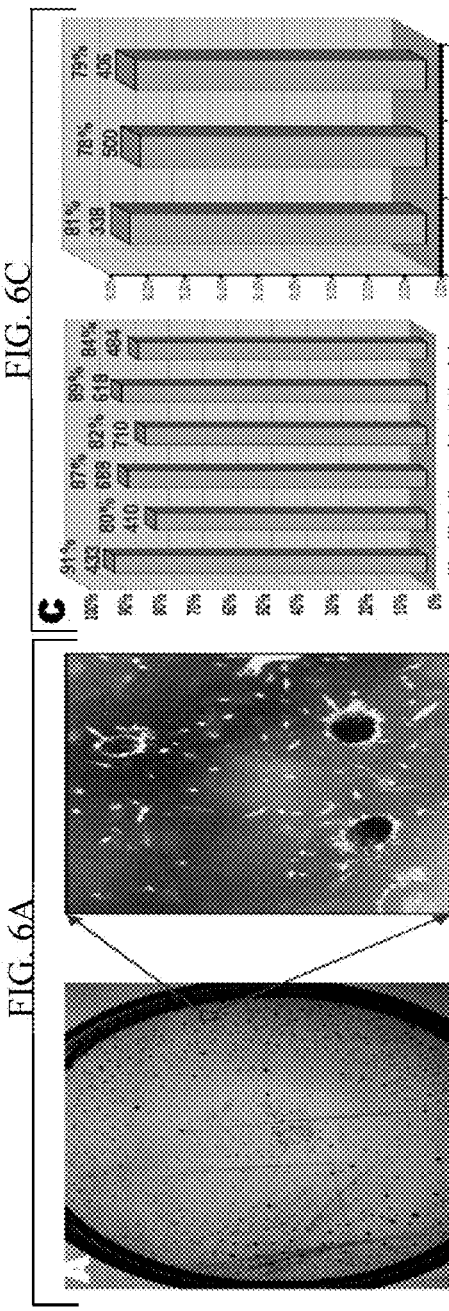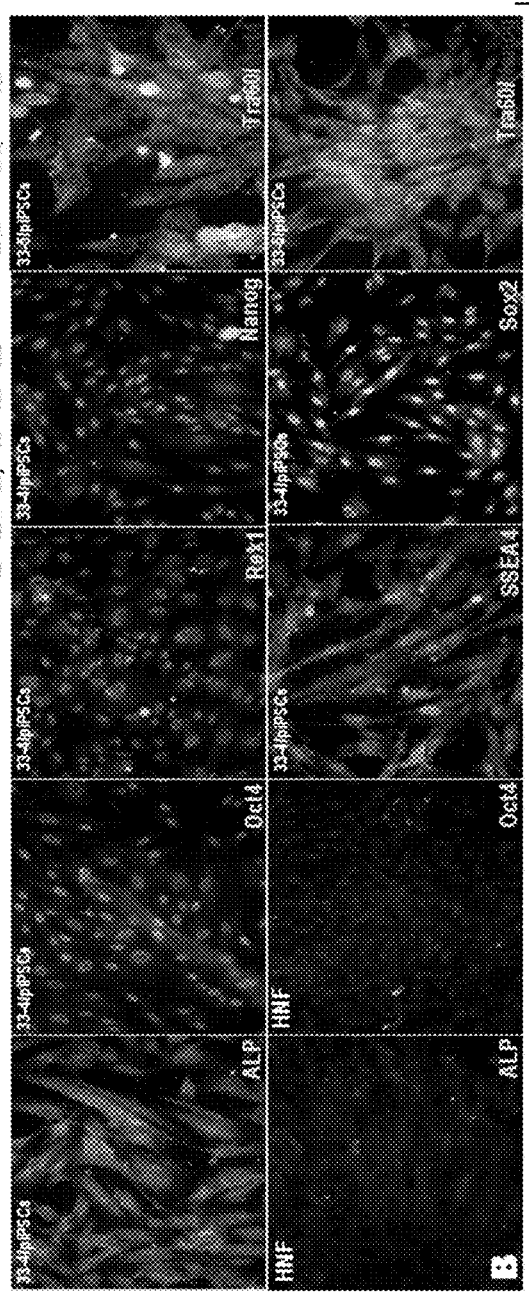
FIG. 6A  FIG. 6C  FIG. 6B

PROTEIN-INDUCED PLURIPOTENT CELL TECHNOLOGY AND USES THEREOF

REFERENCE TO RELATED APPLICATIONS

This application is a divisional of U.S. patent application Ser. No. 14/113,522, filed Feb. 20, 2014, which is a U.S. national stage application of PCT/US2012/036051, filed May 2, 2012, which claims priority to U.S. Provisional Patent Application Ser. No. 61/481,273, filed May 2, 2011. The entire content of each application is incorporated herein by reference.

FIELD OF THE INVENTION

The present invention relates to protein transduction and uses thereof. More specifically, the present invention relates to a protein-induced pluripotent stem cell (piPSC) technology that generate high-quality piPS cells within one week with nearly 100% conversion efficiency and its applications thereof. The present invention also relates to a feeder-free piPSC culture condition and a whole dish expansion without colony picking and clonal expansion and their applications thereof.

BACKGROUND OF THE INVENTION

Embryonic stem (ES) cells are stem cells derived from an embryo. With the present state of technology, the creation of a human embryonic stem cell line requires the destruction of a human embryo, raising a controversial ethical issue for human ES cell research. ES cells are distinguished from other types of cells by two distinctive properties: pluripotency and unlimited self-renewal. Under defined conditions, ES cells are capable of renewing themselves indefinitely, allowing ES cells to be employed as useful tools for both research and regenerative medicine, since we can produce limitless ES cells for continued research or clinical use. ES cells are also able to differentiate into all derivatives of the three primary germ layers: ectoderm, endoderm, and mesoderm, include more than 220 cell types in the adult body. Pluripotency distinguishes ES cells from adult stem cells found in adult tissues; while ES cells can generate all cell types in the body, adult stem cells are multipotent and can only produce a limited number of cell types within this tissue type.

ES cell therapies can be used for regenerative medicine and tissue replacement for injury or disease treatments, such as blood, immune-system and different diseases related genetic diseases, cancers, cardio-vascular disease, juvenile diabetes, Parkinson's and Alzheimer's diseases, wound healing, rheumatoid arthritis, baldness, deafness, blindness, amyotrophic lateral-sclerosis, muscular dystrophy and spinal cord injuries. Besides the ethical concerns of stem cell therapy, there is a technical problem of graft-versus-host disease associated with allogeneic stem cell transplantation. Since the ES cells used for regeneration medicine are from human embryos, immuno-rejection will be always a major problem when transplantation of the ES cells is performed to individual patients for disease treatment. Other potential uses of ES cells include investigation of early human development, study of genetic disease, in vitro systems for toxicology testing and drug screening.

The process for culturing ES cells is quite burdensome. Human ES cells are isolated by transferring the inner cell mass into a plastic laboratory culture dish. The inner surface of the culture dish is typically coated with a feeder layer: mouse embryonic skin cells that have been treated so they will not divide, but provide ES cells a sticky surface attaching to. Feeder cells also release nutrients into the culture medium. Researchers have devised ways to grow embryonic stem cells without mouse feeder cells. This is a significant scientific advance because of the risk that viruses or other macromolecules in the mouse cells may be transmitted to the human cells.

The process for ES cell expansion is also quite time consuming. ES cells form colonies. Usually, the ES cell expansion is first to select individual ES cell colonies and then expand the selected colonies. This significantly slows down the ES cell expansion and may cause higher mutational rate if the selected colonies contain genetic mutations.

In 2006, Shinya Yamanaka and colleagues showed that introduction of four transcription genes: Oct4, Sox2, Klf4 and c-Myc using retroviruses into mouse fibroblasts could generate induced pluripotent stem cells (iPS cells), which display pluripotency. This is a revolutionary discovery since for the first time it is shown that somatic cells can be reprogrammed back to ES-like cells. The iPS cells are believed to be identical to natural ES cells in many aspects, such as the expression of certain stem cell genes and proteins, chromatin methylation patterns, doubling time, embryoid body formation, teratoma formation, viable chimera formation, the unlimited self-new property and differentiability. However, the full extent of their relation to natural pluripotent stem cells is still being assessed.

It is believed that iPS cell technology is less ethically controversial, since this technology allows for generation of pluripotent stem cells without human embryo. This technology may also enable generation of patient specific ES cell lines that could potentially be used for cell replacement therapies to treat various human diseases and allows the generation of ES cell lines from patients with a variety of genetic diseases and will provide invaluable models to study those diseases and for drug screening.

In 2007, several groups showed that the iPS cells generated from mouse fibroblasts via four-gene retroviral delivery produced viable chimera. These groups used Nanog for detection of iPS cells, indicating that Nanog is a major determinant of cellular pluripotency. However, c-Myc is oncogenic and 20% of the chimeric mice developed cancer. In a later study, Yamanaka reported iPSCs could be generated without c-Myc. The process takes longer and is not as efficient, but the resulting chimeras didn't develop cancer.

Also in 2007, iPS cells were generated from human somatic cells, representing a milestone for iPS cell technology. However, the viral transfection systems used inserted the genes at random locations in the host's genome and created major concerns for potential therapeutic applications of these iPSCs, because the created cells might be prone to form tumors. To overcome these dangers, an adenovirus was used to transport the requisite four genes into the genomes of skin and liver cells of mice, resulting in cells identical to embryonic stem cells. Since the adenovirus does not combine any of its own genes with the targeted host, the danger of creating tumors is eliminated, although this method has not yet been tested on human cells. Yamanaka and several other labs have since demonstrated reprogramming can be accomplished via plasmid without any virus transfection system at all, although at very low efficiencies.

In May 2009, two reports by Ding's and Kim's labs reported that both mouse and human iPS cells (piPSCs) were generated by direct delivery of four proteins, which were coded by the four reprogramming genes, thus eliminating the need for viruses or genetic modification of human somatic cells. A recent report further showed that iPSCs could be generated using mRNAs to generate mRNA-induced iPS cells (riPSCs). This solved one of the most challenging safety hurdles associated with personalized stem cell-based medicine and enables scientists to make piPS cells without genetically altering them. Because the proteins do eventually degrade, there should be no trace of their existence in the cells by the time they would be used for experiments or therapies, representing a major breakthrough in the iPS cell technology.

Despite intense worldwide research efforts, the current iPS cell technology still suffers FOUR major problems: 1. Inefficiency; 2. Time consumption; 3. Complex and expensive; and 4. Quality problem.

The current iPS cells technology only converts 0.001-1% somatic cells into iPS cells. For gene delivery using virus vectors, the conversion efficiency from somatic cells to iPS cells could reach 0.1-1%, depending on different starting somatic cells. Using embryonic fibroblast as the starting cells, the conversion efficiency reaches ~1%; however, using adult somatic cells, the conversion efficiency is <0.1%. For gene delivery using non-virus means, this conversion efficiency is <0.1%. The conversion efficiency for human protein-induced iPS cells is extremely low which only reaches 0.001%.

Additionally, the current iPS cell technology, including both gene delivery and protein delivery, usually takes 4-8 weeks to complete reprogramming of human somatic cells into iPS cells and requires many cycles of gene transfection or protein delivery. This makes the current iPS cell technology a complicated and expensive technology. Furthermore, the quality of iPS cells generated by the current iPS cell technology is questionable in terms of resembling human ES cells. These major technical problems block the translation of iPS cells from its human clinical applications.

The main reason that causes these major problems of the current iPS cell technology is due to the technical challenges of gene delivery and protein delivery, which suffer low efficiency and hard to control stoichiometry of the delivered genes with multiple gene/protein delivery. For iPS cell generation, one has to deliver four genes or four proteins simultaneously into nuclei of somatic cells to turn on the intracellular auto-regulatory circuits that initiates the "stem gene expressions" and silences the "somatic gene expressions", thus somatic cells can be converted into embryonic stem-like cells.

It is common knowledge that the current gene delivery technology, including both virus vector and non-virus approaches, suffers low efficiency problem for four-gene delivery simultaneously. In addition, there is no guaranty that all four genes are delivered inside cells at an equal stoichiometry. In most cases, the four-gene delivery is random, depending on different delivery vehicles used. To solve this problem, an alternative approach has been developed that inserts all four genes into one virus vector with different linkers between each gene. In this case, only one virus vector is required to be delivered into somatic cells for iPS cell generation, enhanced the delivery efficiency. However, even with this approach, a maximum of iPS cell conversion efficiency is achieved only ~1% for adult somatic cells and could reach <5% for embryonic somatic cells.

In addition to low efficiency of gene delivery, this approach also suffers another problem: time consuming. Once the reprogramming genes have been delivered, they traffic randomly inside cells and only a small fraction of the genes can reach to nuclei. However, only those somatic cells that have the delivery genes located inside nuclei can be reprogrammed to generate iPS cells. This further significantly reduced the iPS cell conversion efficiency, in order to solve this problem, repeated gene transfection has been performed to enhance the random probability of nuclear incorporation of delivered genes, which is time consuming. It takes 7-14 days for the delivered genes to start expressions and ~30 days to observe non-iPS cell colony formation. To complete reprogramming, it usually takes 4-8 weeks to generate iPS cells from human adult somatic cells.

For protein-induced cell reprogramming, one has to deliver proteins into the nuclei of fibroblasts. Both Ding's and Kim's labs engineered the reprogramming proteins by adding a cell-penetrating peptide (CPP, 9R-11R) into the C-terminus. Although the CPP-fusion method delivers the reprogramming proteins into the cells, several major drawbacks of the CPP-based protein delivery do exist:

(1) The CPP-fusion has a high risk of altering the properties/functions of reprogramming proteins.
(2) The CPP has low protein delivery efficiency.
(3) The CPP-delivered proteins are sensitive to intracellular proteases since CPP is peptide based, causing degradation of the delivered proteins.
(4) The CPP does not have a targeting capability to nuclei for proteins to initiate reprogramming.

Once the proteins are inside cytosol, the intracellular proteases will first try to degrade them if they are not folded properly. For those proteins that survived intracellular protease degradation, they will randomly collide with different intracellular compartments and only a very small fraction of proteins can reach nuclei to initiate protein-induced reprogramming. To enhance the probability of nuclei location of the reprogramming proteins, both Ding's and Kim's lab adopted a repeated circles (7-10 cycles) of protein delivery.

These major drawbacks cause extremely low efficiency of somatic cell conversion into iPS cells (<0.005%). In addition, it also took a long time for protein initiated reprogramming of fibroblast cells into iPS cells. In Ding's paper, it took 5 weeks to observe iPS cell colony formation from mouse embryonic fibroblast, which is much easy to reprogram into iPS cells as compared with human adult fibroblast. When human newborn fibroblasts were used by Kim et al to generate iPS cells, it took 8 weeks to observe iPS cell colony.

As discussed above, lack of delivery efficiency, lack of nuclear targeting/random nature of intracellular trafficking and long process of the current gene and protein delivery technology make it very hard to control the quality of the generate iPS cells. This is demonstrated by several recent reports, indicating that the newly generated iPS cells display distinct patterns of gene expression from those of human ES cells. However, the iPS cells display a very similar gene expression pattern as human ES cells after 50-60 passages. Based on this results, a continue reprogramming concept has been proposed during continue passage of iPS cells. Unfortunately, it was also observed that at later passages (50-60 passages), the iPS cells display major chromosomal changes as compared with the starting somatic cells, making it impossible to use these IPS cells for human clinical application.

It would therefore be beneficial to develop an iPS cell technology that can generate high-quality iPS cells from human adult somatic cells within a few days at near 100% conversion efficiency.

SUMMARY OF THE INVENTION

According to the present invention there is provided a piPSC technology which can generate high-quality piPS cells from different starting somatic cells directly using bacterial expressed, recombinant reprogramming proteins.

The present invention provides a piPSC technique that utilizes a QQ-protein delivery technique that enables targeted delivery of the reprogramming protein directly into the nuclei of human somatic cells within the first hour after delivery. This initiates cell reprogramming of somatic cells in 12-hours and completes cell reprogramming within one week to generate piPS cells.

The present invention provides piPSC procedures that generate mouse, rat and human piPS cells from adult fibroblasts and other somatic cells with near 100% conversion efficiency.

The present invention provides procedures to generate high-quality iPS cells from many different somatic cells, including mouse primary fibroblasts, adult mouse fibroblasts, human newborn fibroblasts, human primary adult fibroblasts, human adult keratinocytes and human amniotic fluid.

The present invention also provides the procedures to generate high-quality iPS cells from different diseased somatic cells, including rat tumor cells, such as 9 L-glioma cells, mouse metastatic breast cancer cells, such as 4T1-cells, human breast cancer cell lines, such as MDA-MB-231, human brain tumor cell lines, such as U87 and U251-glioma cells, human primary Stage 4 GBM cells, human primary fibroblasts from Alzheimer patients with apoE3 or apoE4 isoforms.

The present invention provides a piPSC technology that is simple and only involves one-step of incubation of somatic cells with reprogramming proteins, either four reprogramming proteins (Oct4/Sox2/Klf4/c-Myc), or three reprogramming proteins (Oct4/Sox2/Klf4), or two reprogramming proteins (Oct4/Sox2), or only one reprogramming proteins (Oct4).

The present invention also use other reprogramming protein combinations, such as Sox2, Oct4 and Nanog (SON), in addition to the traditional Yamanaka's four transcription factors (Oct4/Sox2/Klf4/c-Myc), to generate piPSCs within 1 week at near 100% efficiency. Since Klf4 and c-Myc are oncogenic proteins and the SON factors are the master regulator for pluripotency, cell reprogramming using the SON factors may significant reduce the mutation rates and significantly enhance the quality of the generated piPSCs that is safe for human clinical applications.

The present invention describes a feeder-free piPSC culture condition that focuses on monolayer piPSC culture for long-term self-renewal of piPSCs. This feeder-free piPSC culture condition avoids mouse feeder layer and solves the major safety concern of the possible cross species contamination of the generated piPSCs for future safe human clinical applications.

The present invention describes a monolayer whole dish passaging method that eliminates colony selection and clonal expansion of traditional iPS cell generation and expansion, significantly enhancing the quality of the generated piPS cells and accelerating piPS cell expansion.

These and other objects, advantages and features of the invention will be more fully understood and appreciated by reference to the description of the current embodiment and the drawings.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 also gives the concentrations of four reprogramming proteins used in cell reprogramming. FIG. 1 further describes cell reprogramming cycles;

FIG. 2A shows the bacterial expression methods used to produce four reprogramming proteins, including both traditional IPTG-induction method and high cell-density iPTG-induction method. These methods include key steps and parameters used in the bacterial expression. Top Right Panel is a Table of the optimized recipes of the medium that are used in the bacterial expression;

FIG. 2B shows the SDS-PAGE and western blot of the purified reprogramming proteins for Oct4, Sox2, Kf4 and c-Myc. The yields of the bacterial expression of these four reprogramming proteins are between 80-120 mg/liter;

FIG. 5A shows a microscopic image of piPSC colonies six days after reprogramming with four proteins, showing many piPSC colonies in this small view area in a feeder-free medium. In general, there were observed 500-1500 piPSC colonies in one cell culture dish;

FIG. 5B shows an enlarged view of one piPSC colony, showing clear edge;

FIG. 5C shows human newborn fibroblast (HNF) was cultured for 24 hours without reprogramming protein, serving as a negative control. This panel only shows nuclei of HNF by DAPI staining without ALP stain;

FIG. 5D shows HNF was cultured with four reprogramming proteins for 3 hours and then switched to a medium without reprogramming proteins;

FIG. 5E shows HNF was cultured with four reprogramming proteins for 5 hours and then switched to a medium without reprogramming proteins;

FIG. 5F shows HNF was cultured with four reprogramming proteins for 24 hours at a lower protein concentration (0.5 μg/ml). The samples were treated with ALP kits for enzymatic reaction and stained in red fluorescence for ALP protein expression. Panels C-F indicates that the reprogramming condition can be optimized for the best conversion efficiency of piPS cells from HNF. Only ~30% of cells showed strong ALP staining in D, whereas the rest of the cells showed either no or weak ALP staining. When a 5-hour protein reprogramming was performed, significantly more cells (60%) showed strong ALP staining, although cells with weak and no ALP staining were still observed (40%). Experimental conditions were optimized by incubating HNF with a lower concentration of the four reprogramming proteins for 24 hrs (F). Virtually every cell was ALP-positive under this condition, suggesting that cell reprogramming of every single cell is initiated and that it is possible to generate piPS cells under this one-cycle reprogramming condition;

FIG. 6A shows a dish of piPSC colonies at the first passage of #33 reprogramming (Left) and a zoomed-in view of the boxed area, showing red piPSC colonies. The colonies were stained with ALP (red);

FIG. 6B shows fluorescence images of single immunostains (Left Panels) and double immunostains (Right) of monolayer piPSCs using different pluripotency markers as labeled in each panel. For double stains, we considered positive stained cells only when both surface and nuclear markers were positive. For those cells that only nuclear or surface marker was positive stained, we considered that they were negative. Negative controls of immunostains using the starting HNF were also performed and displayed. ALP and SSEA4 are surface markers and Oct4, Sox2, Nanog and Rex1 are nuclei markers;

FIG. 6C shows bar diagrams showing the conversion efficiency of the piPSC technique based on six single immunostains (Left) and three double stains (Right). By manually counting the positive and negative stains of more than 300 cells, conversion efficiency was calculated. On the top of each bar, the upper red number is the conversion efficiency and the lower blue number is the number of cells that were counted for calculation of the corresponding conversion efficiency;

FIG. 11A shows Right: Heatmaps (log 2) of the TagMan® Stem Cell Pluripotency Arrays for gene expression in IPS cells at Passenge-1 and passenger-5 as compared to those of the starting HNFs. Single TaqMan® real-time RT-PCR was further used to confirm the array data. Left: A bar diagram of q RT-PCR to assess gene expression of Oct4, Sox2, and Nanog in piPSC at 1 and 5 passages and HNF cells. Relative gene expression represents fold changes (log 2) relative to that of HNF cells;

FIG. 11B shows SKY chromosome analysis was performed for HNF ($17^{th}$ passage) and piPSCs ($10^{m}$ passage), showing the same karyotype between the generated piPS cells and the parental HNF cells;

FIG. 11C shows Western blot result of the key pluripotent proteins, including three master regulators (Oct4, Sox2 and Nanog) and one late pluripotent marker (Rex1), of piPSCs ($5^{th}$ passage) and starting HNF (Right). A housekeeping protein (Actin) shows that equal amount of piPSCs and HNF cells were used for these western blots;

FIG. 11D shows demethylation of the Nanog gene of the piPSCs (~85%, #$33^{rd}$ reprogramming, $2^{nd}$ passage) and NHF (~15%);

FIG. 12A shows neural (Nestin, ectodermal);

FIG. 12B shows muscle and endothelial-like (Desmin, mesodermal);

FIG. 12C shows endoderm-like cells (AFP, endoderm;

FIG. 12D shows neurons (Tuj1+, white arrow);

FIG. 12E shows Type I astrocytes (GFAP+);

FIG. 12F shows Type II astrocytes (GFPA+);

FIG. 12G shows Oligodendrocytes (OI+);

FIG. 12H shows neural stem cells (Sox2+);

FIG. 12I shows neural stem cells (Nestin+). Significant cell morphological differences are observed in all panels. However, cells in FIGS. 12D, 12E, 12F and 12G display typical neuron/astrocyte/oligodendrocyte morphologies and cells in FIGS. 12H and 12I display typical neural stem cell morphology, confirming that the immunostains are NOT false positive;

DETAILED DESCRIPTION OF THE INVENTION

Figure 1:
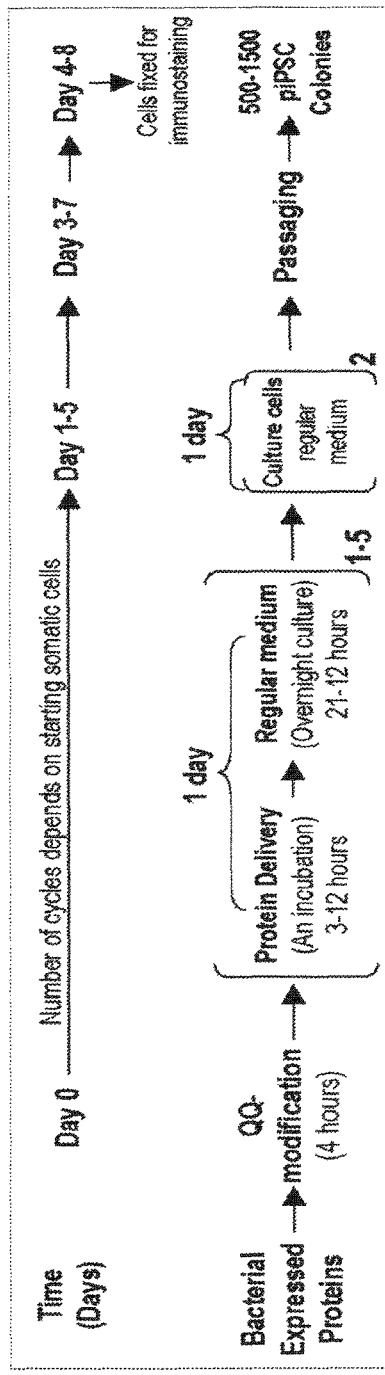
FIG. 1 is a flow chart depicting the protocol of the present invention, showing an outline of each step of this piPSC technology.

The present invention provides a protein induced piuripotent stem cell (piPSC) technology. The present invention provides the use of this piPSC technology which can generate high-quality iPS cells from different starting somatic cells directly using bacterial expressed, recombinant reprogramming proteins.

The piPSC technology of the present invention is simple and only involves one-step of incubation of somatic cells with reprogramming proteins. The reprogramming proteins can be any proteins known to those of skill in the art to be capable of performing the recited function. Examples of such proteins include, but are not limited to, four reprogramming proteins (Oct4/Sox2/Klf4/c-Myc), or three reprogramming proteins (Oct4/Sox2/Klf4), or two reprogramming proteins (Oct4/Sox2), or only one reprogramming proteins (Oct4).

The piPSC technology of the present invention also use other reprogramming protein combinations, such as Sox2, Oct4 and Nanog (SON), or Nanog/Oct4, or Nanog only, in addition to the traditional Yamanaka's four transcription factors (Oct4/Sox2/Klf4/c-Myc), to generate piPSCs. Since Klf4 and c-Myc are oncogenic proteins and the SON factors are the master regulator for pluripotency, cell reprogramming using the SON factors can reduce the mutation rates and significantly enhance the quality of the generated piPSCs that is safe for human clinical applications.

The piPSC technology of the present invention utilizes a QQ-protein delivery technique that enables targeted delivery of the reprogramming protein directly into the nuclei of human somatic cells within the first hour after delivery. This initiates cell reprogramming of somatic cells in 12-hours and completes cell reprogramming within one week to generate piPS cells. Additionally, the procedures generate mouse, rat and human piPS cells from adult fibroblasts and other somatic cells with near 100% conversion efficiency.

The piPSC technology provides a universal procedure that not only can be used to efficiently generate protein-induced pluripotent stem cells with the Yamanaka's factors or the SON factors, but also can be broadly used to generate adult stem cells, such as neural stem cells, epithelial stem cells, skin stem cells, mesenchymal stem cells and hematopoietic stem cells, as well as trans-differentiations to directly generate cardiomyocytes, neuron, brown adipocytes, insulin secretion cells and other types of terminal differentiated cells from adult somatic cells using different sets of reprogramming proteins.

The piPSC technology can be used to generate high-quality iPS cells from many different somatic cells, including but not limit to; mouse primary fibroblasts of healthy animals, adult mouse fibroblasts, human newborn fibroblasts, human primary adult fibroblasts, human adult keratinocytes and human amniotic fluid. High-quality iPS cells can also be generated from different diseased somatic cells, including but not limited to: rat tumor cells, such as 9 L-glioma cells, mouse metastatic breast cancer cells, such as 4T1-cells, human breast cancer cell lines, such as MDA-MB-231, human brain tumor cell lines, such as U87 and U251-glioma cells, human primary Stage 4 GBM cells, human primary fibroblasts from Alzheimer patients with apoE3 and apoE4 isoforms.

The present invention describes a feeder-free piPSC culture condition that focuses on monolayer piPSC culture for long-term self-renewal of piPSCs. This feeder-free piPSC culture condition avoids mouse feeder layer and solves one of the major safety concerns of the possible cross species contamination of the generated piPSCs for future safe human clinical applications.

The present invention describes a new piPSC passaging method: whole dish passaging, for long-term self-renewal and expansion of piPSCs, since the conversion efficiency of this piPSC technology reaches near 100%. This new piPSC passaging method focus on passaging and expansion of monolayer piPSCs and it is simple and fast. It also avoids colony selection during cell reprogramming, colony picking and clonal expansion, may significantly reduce the mutation rates and enhance the quality of the generated piPSCs that is safe for human clinical applications.

The present invention can be used to produce large amount bacterial expressed recombinant reprogramming proteins, including but not limiting to: Oct4, Sox2, Klf4, c-Myc, Lin28, Nanog, BMP4 and other reprogramming proteins.

More specifically, the present invention is based on the QQ-protein transduction technology and an in vivo refolding technology as disclosed in U.S. Pat. No. 8,722,348, incorporated herein by reference. The QQ reagents have the ability of delivering multiple proteins simultaneously or consecutively into cells at near millimolar concentration and the capability of targeted delivery of proteins into the corrected intracellular compartments. In addition, QQ-reagents protect proteins from proteases inside cells. The delivered proteins are properly refolded and post-translationally modified by the intracellular machinery and follow the same intracellular trafficking and secretion pathways as their endogenous counterparts. Thus, the QQ-protein transduction is a physiologically relevant protein transduction technology.

The present invention extends the QQ-protein delivery to piPS cell technology by optimization of the QQ-reagent recipe. The new recipe efficiently delivers reprogramming proteins into nuclei of the starting somatic cells. Accordingly, the amount of modification of target proteins with the new recipe can be adjusted by altering the QQ-compositions to obtain the best delivery efficiency into different somatic cells for specific reprogramming proteins for cell reprogramming.

The present invention also provides direct experimental evidence that cell reprogramming can be initiated within several hours after QQ-protein delivery, thus the pluripotent genes start to endogenously be expressed during this period of time. Additionally, the present invention also provides direct experimental evidence that cell reprogramming can be completed within 1 week after QQ-protein delivery, thus the genes of the completed reprogramming markers start to endogenously expressed during this period of time.

The method and products of the present invention are an efficient and flexible way to optimize the composition and concentrations of reprogramming proteins for optimization of the quality of generated iPS cells using QQ-protein delivery.

Another benefit is that the piPSC technology presented here generates tissue-specific piPS cells using reprogramming proteins without genetic manipulations of the parental cells. In addition, this piPSC technology uses the "SON" proteins, the master ESC regulators, for cell reprogramming, and removes the oncogenic KLF4 and c-MYC proteins, solving the major safety hurdles for future human clinical applications for a possible personalized disease therapy.

The piPSC technology can be used in human clinic applications, including regeneration medicine and cell replacement therapy, generation of the iPS cell banks from individual patients with genetic disorders, disease models based on piPS cells from individual patients and testing of efficacy of different drugs, including small molecule drugs, protein drugs, DNA drugs, RNA drugs, carbonhydrate drugs and lipid-based drugs.

The present invention describes the application of this piPSC technology in human clinic applications to treat different human diseases, including, but not limited to, cancer, heart diseases, strokes, diabetes, obesity, Alzheimer's diseases, Parkinson's disease, amyotrophic lateral-sclerosis, myocardial infaction, muscular dystrophy, CMT-1A, spinal cord injury, traumatic brain injury, learning defects, missing teeth, wound healing, bone marrow translantation, osteoarthritis, rheumatoid arthritis, baldness, blindness, deafness, Crohn's disease and genetic diseases, and other similar diseases.

Most importantly, greater than 85±4% conversion efficiency has been achieved. The generated piPSCs display characteristics of human embryonic stem cells (hESCs) and can be expanded stably and homogenously for 6-months under a feeder-free condition. These piPSCs also have the potential to differentiate into the three germ layers both in vitro and in vivo.

Such an efficiency of this piPSC technology is based on a state-of-the-art QQ-protein delivery technology. The QQ-reagent protects the delivered proteins from degradation by intracellular proteases and has targeting capability to specific intracellular compartments based on the signal sequences carried by the delivered proteins. The QQ-delivery was applied to protein-induced cell reprogramming of HNFs, which generated piPSCs within 1 week with greater than 85±4% conversion efficiency. Such high conversion efficiency allows for elimination of the colony selection during cell reprogramming and clonal expansion for maintaining a pure population of piPSCs, thus dramatically speeding up the entire procedure of piPSC generation and expansion. A method of monolayer piPSC passaging was developed using a feeder-free condition for expansion of the generated piPSCs. This piPSC technology may also significantly enhance the quality of piPSCs for safe human clinical applications by reduction of the mutation rates during traditional colony picking and clonal expansion.

The piPSC technology of the present invention includes a very high efficient bacterial expression method that can be used to produce pure reprogramming proteins at a very high yield (80-120 mg/liter) and the recipes of the media that was used for bacterial expression. This significantly reduced the cost of this piPSC technology.

The piPSC technology of the present invention utilizes an in vivo protein refolding technology, which directly delivers the bacterial expressed reprogramming proteins into the somatic cells using the QQ-protein delivery technology for refolding by the mammalian cellular folding machinery. Thus, this piPSC technology skips the step of complicated and inefficient in vitro protein refolding of the bacterial expressed reprogramming proteins, thus making this piPSC technology a much simple and inexpensive technology.

The piPSC technology of the present invention utilizes QQ-protein delivery technology to directly deliver reprogramming proteins into the nuclei of somatic cells to initiate and maintaining cell reprogramming. There has been shown that this piPSC technology could specifically deliver reprogramming protein into the nuclei of virtually every single somatic cell in 1.5 hour after QQ-protein delivery.

The piPSC technology of the present invention can also initiate cell reprogramming in first 24 hours after protein delivery and the cell reprogramming could be completed in 5 days to generate piPS cells, which for the first time demonstrates that cell reprogramming is not a stochastic process, but defined and repeatable process to generate piPS cells from somatic cells using QQ-protein delivery technology.

The piPSC technology of the present invention includes a feeder-free cell culture condition to passage the generated piPSCs. Described herein is the detailed procedure of this feeder-free condition and also reported the potential colony changes in shape and morphology. Using this feeder-free condition, more than 30 passages of the generated piPS cells have successfully passed for more than 6 months.

The piPSC technology of the present invention describes a passaging method which is distinctly different from the traditional passaging method that picks up a single colony for passaging. Since this piPSC technology converts nearly 100% somatic cells into piPS cells, there was developed a whole dish passaging method that passes the cells of the whole dish into new dishes for passaging. This allows one to avoid colony picking and clonal expansion and may significantly reduce the mutation rates of the generated piPS cells. This solved the major problem of generation of enough piPS cells for applications and may significantly enhance the quality of piPS cells for safe human clinical applications.

The piPSC technology of the present invention suggests a procedure for developing disease models for individual patients. This is one of the important applications of this piPSC technology that allows one to study human diseases in a dish.

The piPSC technology of the present invention suggests a procedure for drug screen and toxicity test of the drugs for individual patients. This is another important application of this piPSC technology that potentially allows one to develop new drugs in a dish on an individual patient basis.

The piPSC technology of the present invention suggests a patient-based stem cell therapy to treat human diseases, including but not limit to Alzheimer's disease, Parkinson's disease, stroke, learning defects, traumatic brain injury, would healing, spinal cord injury, osteoarthritis, rheumatoid arthritis, Crohn's disease, multiple sites cancers, diabetes, muscular dystrophy, myocardial ufraction, amyotrophic lateral sclerosis, baldness, blindness and deafness. This is the most important application of this piPSC technology that potentially allows us to treat many human diseases on an individual patient basis.

Three technologies were developed to solve the most challenging problems of the previously available or current iPSC technology. These technologies include an efficient bacterial expression system, allowing a gram/liter quantity of pure recombinant protein production; An in vivo protein refolding technique to efficiently refold bacterial expressed proteins using intracellular folding machinery of mammalian cells; and the QQ-protein transduction technology that has a targeting capability to specific intracellular organelles, including nucleus.

Using the first technology, there were prepared bacterial expressed Oct4, Sox2, Klf4 and c-Myc proteins at yields of 80-120 mg per one-liter expression, which are confirmed by western blots. This makes recombinant reprogramming protein much cheaper and affordable. The second technology—an in vivo protein refolding technology allows one to skip the in vitro refolding step adopted by Ding et al, which is inefficient, expensive and complicated. Generally, this method delivers the bacterial expressed proteins into mammalian cells using the QQ-protein delivery technology. The intracellular folding machinery could efficiently refold the bacterial expressed proteins.

The Third technology is an advanced QQ-protein delivery technology, which has several features, ensuring the physiological relevance of this protein delivery technology:

(1) QQ-reagent non-covalently associates with proteins and no tags are added to the delivered proteins.
(2) QQ-reagent masks/protects the delivered proteins from intracellular proteases (high metabolic stability).
(3) QQ-reagent specifically delivers proteins to their target compartment based on the sequence localization signals carried by the delivered proteins (Targeting capability).
(4) QQ-reagent has a high efficiency of protein delivery, up to millimolar (mM) intracellular concentration.

The QQ-reagents are polyethyleneimine (PEi)-based cocktails, with other key ingredients, such as lipids and enhancers. They can be formulated for specific applications. The QQ-reagent binds to the delivered proteins non-covalently, which coats a layer of the QQ-reagent on the surface of the delivered protein. This MASKS the protein from intracellular protease degradation. The QQ-reagent DOES gradually dissociate from the delivered proteins once inside the cells. These unique features of the QQ-reagents make the delivered proteins indistinguishable from their endogenous counterparts inside the cells. Once the delivered proteins reach their targeted compartments, the cell's machinery behaves as if they were the endogenous counterparts. It was demonstrated that the QQ-delivered proteins folds and post-translationai modifies properly inside the cells and they follows the identical intracellular trafficking and secretion pathway as their endogenous counterparts.

A patent application, incorporated herein by reference, of the QQ-protein delivery technology and the in vivo protein refolding technology has been submitted on May 28, 2008. These three advanced technologies SOLVED the major problems of the current iPSC technology. This allows the development of a piPSC technology, for generating high-quality iPS cells from many different somatic cells using reprogramming proteins within 1 week with near 100% conversion efficiency. In addition, the iPSC technology is a simple and affordable technology.

More specifically, using the state-of-the-art QQ-protein delivery technique, the bacterial expressed recombinant reprogramming proteins are directly delivered into the nucleus of virtually every starting human newborn fibroblast (HNF). The recombinant reprogramming proteins are properly refolded by the intracellular folding machinery and initiate cell reprogramming within 24 hours after protein delivery. This cell reprogramming is well maintained and can be completed within 1 week. The generated piPSCs display characteristics of human embryonic stem cells (ESCs), can be expanded stably and homogenously for over 30 generations in a feeder-free condition and have the differentiation potentials both in vitro and in vivo into three major germ layers. Most importantly, this piPSC technique generates piPSCs from HNFs with great than 85±4% conversion efficiency. Such a high reprogramming efficiency may significantly enhance the quality of the generated piPSCs that are safe for future human clinical applications.

The Examples below are included to demonstrate preferred embodiments of the invention. It should be appreciated by those of skill in the art that the techniques disclosed in the Examples represent techniques and compositions discovered by the inventors to function well in the practice of embodiments disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of embodiments disclosed herein.

EXAMPLES

Materials and Methods

Plasmids Construction.

Four genes, Oct4 (NP_002692), Sox2 (NP_003097), Klf4 (NP_004226), Nanog (NM_024865.2) and c-Myc (NP_002458), were subcloned into a sHT-pET30a bacterial expression vector, in which a short his-tag: 'HHHHHHSS' (SEQ ID NO: 1) replaced the long his-tag. A factor Xa (IEGR) cleavage site is between the short his-tag and the coding genes. The sequences of the bacterial expression vectors were confirmed by DNA sequencing.

Protein Expression and Purification.

The DNA constructs of reprogramming proteins were transformed into E. Coli strain BL-21 (DE3) individually. A single colony was selected for bacterial protein expression. After brief optimization, protein expressions were induced by 0.5 mM IPTG and continued to culture at 18° C. for 16 hours. The cells were harvested in the binding buffer containing 6M urea and sonicated three times. The recombinant proteins were purified using a His-Bind Resin column (Novagen) according to the manual with modifications. The purified proteins were dialyzed against water and lyophilized into protein powders.

QQ-Modification.

The reprogramming proteins were dissolved in 50 mM sodium phosphate pH 7.4 with 2 M urea. QQ-regents were freshly prepared based on the recipe. Briefly, the QQ-reagent is a cocktail of polyethyleneimine (PEI) 2,000 (2K, 0.2-1.0 mg/ml) and DOTAP/DOPE (25-50 µg/ml). The QQ-modification of reprogramming proteins was performed by mixing the QQ-cocktail with a protein (Oct4/Sox2: 1 mg/ml; Klf4/c-Myc: 0.5 mg/ml; Nanog: 1 mg/ml) for 4-hours at room temperature or overnight in a cold room.

Cell Culture and Cell Reprogramming.

HNFs were cultured on a 35×10-mm cell culture dish till 70-80% confluent (5×10⁴ cells) in the DMEM medium with 10% FBS. The QQ-modified reprogramming proteins were also mixed with DMEM medium with 10% FBS (Invitrogen) and incubated at room temperature for 10 minutes. The final concentration of Oct4, Sox2 and Klf4 were 0.2-0.5 µg/ml while c-Myc was 0.02-0.05 µg ml. To start reprogram, the cell culture medium was replaced by the reprogramming medium (DMEM medium with 10% FBS, 0.1 mM non-essential amino acids, and 2 mM L-glutamine). The protein concentration was gradually reduced as the following: In cycle 1, Oct4/Sox2/Klf4 were 0.5 µg/ml and c-Myc was 0.05 µg/ml. In cycle 2, protein concentration was reduced by half. In cycle 3, protein concentration was further reduced by half. Each cycle contained 3-12 hour incubation with QQ-modified proteins, plus 12-21 hour incubation without reprogramming proteins. After 3 cycles, the cells were cultured in DMEM medium with 20% KSR, 0.1 mM 2-ME, 2 mM L-glutamine, 0.1 mM non-essential amino acids, supplemented with 10 ng/ml bFGF (Stemgent) for post-reprogramming culture for 48-hours. This 48-hour post-reprogramming culture medium was saved as the conditional medium. At the end of post-reprogramming culture, the cells were completely confluent. A confluent dish after post-reprogramming culture would promote the colony formation in a feeder free condition.

Generation of piPSCs Under a Feeder-Free Condition.

A new dish (0.2% gelatin coated) was pretreated with the conditional medium for 15 minutes. The reprogrammed cells were dissociated as monolayer cell suspension using trypsin (0.05%) and transferred into the new dishes. The cells were cultured in a medium that contained Knockout DMEM with 20% KSR (Invitrogen), 10 ng/ml bFGF, 0.2 mM 2-ME (Sigma), 0.1 mM non-essential amino acid (Invitrogen) and 2 mM L-glutamin (Invitrogen). The next day, hundreds of clear edged colonies were observed. The cells were passaged every 5-7 days when the dish was 80-90% confluent. To compare pluripotency of the piPSC populations, either a single piPSC colony was picked for passaging (single colony passaging) or the cells of half a dish were passaged (whole dish passaging). Cell expansion was continued using both passaging methods for up to $10^{th}$ passage (2 months) and immunostaining was performed. During piPSC passaging, medium was changed every other day by replacing half of the medium with fresh feeder-free medium. Feeder-free medium was prepared every other week and kept it in a cold room.

Dosage of Reprogramming Proteins Versus piPSC Colony Formation.

Different concentrations of reprogramming proteins were used to generate piPSC colonies. A two-cycle reprogramming was performed in triplicate at each protein concentration. After reprogramming and post reprogramming incubation (48 hour), the whole dish was passaged into 60×15 mm dishes. The number of colonies was counted under a microscope for three consecutive days starting at passage 2.

Nuclear Targeting of Reprogramming Proteins.

HNFs were seeded into 4 wells one day before experiment. HNFs were incubated with QQ-modified Oct4, Sox2, Klf4 and c-Myc (1-µg/ml) individually for 1.5 hours at 37° C. The cells were washed with PBS 3 times and fixed with 4% formaldehyde then washed 3 times with PBS. The cells were blocked and permeabilized with 2% sheep serum containing 0.2% triton for 2 hours and incubated with primary antibodies with 2% sheep serum PBS overnight in a cold room. Cells were washed 3-times with 1% serum and then incubated with secondary antibodies (1:300 dilution) at room temperature for 2 hours. Cells were washed 3 times using 1% serum-PBS and subjected to fluorescence imaging.

Human Stem Cell Pluripotency Gene Array Analysis.

Total RNA was extracted from HNFs and iPSCs at $1^{st}$ and $5^{th}$ passages using the mirVana miRNA isolation kit (Ambion, USA). TaqMan® Stem Cell Pluripotency Arrays (Applied Biosystems, Foster City, Calif., USA), containing 92 well-defined validated genes, were used for gene expression analysis. Reverse transcription reaction, real-time RT-PCR and data analysis to obtain Ct values were performed according to the manufacturer's protocol. Briefly, cDNA was reversely transcribed from 1.0 ug total RNA, respectively, using random primers from the High Capacity cDNA Archive Kit (Applied Biosystems). RT-PCR was carried out on an ABI Veriti Thermal cycler (Applied Biosystems). 500 ng of cDNA was mixed with TaqMan® Universal PCR Master Mix per reservoir, two reservoir for each sample. The sample-specific PCR mix was loaded into the TaqMan® Stem Cell Pluripotency Array, each reservoir 100 ul. After centrifuge, the TaqMan array was then run on a 7900HT system (Applied Biosystems) for quantitative real-time PCR analysis. Raw Ct values were calculated using the SDS software version 2.3 and RQ manager 1.2 (Applied Biosystems) applying automatic baseline settings and a threshold of 0.05. For array data analysis, only those miRNAs with a Ct value equal to or below 36 were taken into account. Raw Ct values were imported into RealTime StatMiner 4.2 (Integromics, Inc.). GAPDH was selected as endogenous control gene to determine the relative expression of the candidate genes. Gene expressions of HNFs were chosen as calibrator to identify the differentially expressed specific markers of piPSCs. The $-\Delta\Delta Ct$ was calculated and heat map analysis was performed with hierarchical clustering. Single TaqMan® real-time RT-PCR was further used to confirm the array data.

Real-Time RT-PCR.

Total RNA was isolated from the human newborn fibroblast and piPSCs ($1^{st}$ and $5^{th}$ passages) using the mirVana miRNA isolation kit (Ambion, USA) according to the manufacturer's specifications. For each RT reaction, 200 ng RNA was used for cDNA syntheses using High-Capacity cDNA Reverse Transcription kits (Applied Biosystem, USA). PCR reaction was done in the HT-7900 system. Results were the average measured in triplicate and normalized to a control gene GAPDH. The relative expression of target genes was calculated using the comparative threshold cycle method. Expression differences were generated by calculating $-\Delta\Delta Ct$.

Western blot.

The purified proteins or piPSC lysates were separated by 10% SDS-PAGE in reducing conditions and blotted onto nitrocellulose membrane. The antibodies against human Oct4 (Santa Cruz), Sox2 (Santa Cruz), KLF4 (R&D SYSTEMS) and c-Myc (R&D SYSTEMS) were used to detect the proteins. Secondary antibodies against mouse IgG (Santa Cruz), Rabbit IgG (Santa Cruz) and Goat IgG (Sigma) were used respectively. The protein signals were detected by SuperSignal West Pigmo Chemiluminescent Substrate (Thermo Scientific, USA).

Embryonic Body (EB) Formation and Spontaneous In Vitro Differentiation.

piPSCs were trypsinized into monolayer cells and cultured in suspension on low adhesion plates (Corning) in DMEM medium with 10% FBS, containing 0.1 mM 2-ME. EBs were observed in several days in suspension. For spontaneous differentiation, medium was changed every 2 days for 10 to 15 days. Spontaneous differentiations were examined by immunostaining of representative lineage specific markers with indicated antibodies. For specific neural linage differentiation, medium was changed to a neural inducing medium at day 3 after EB formation: DMEM with 5% FBS containing 20 ng/ml neural growth factor (PROSpect). For specific cardiomyocyte linage differentiation, medium was changed to a special medium at day 3 after EB formation.

Cytochemistry and Immuno Fluorescence Assay.

ALP assay (Vector Red ALP substrate Kit I) was performed according to manufacturer. Immunocytochemistry was performed using standard protocol for pluripotency and differentiation markers. Briefly, piPSCs and HNFs were seeded in 8-well culture chambers and fixed with 4% paraformdehyde (Sigma), washed three times with PBS. The cells were incubated in 0.2% tritonX and 5% sheep serum (Sigma) for 2 hours at room temperature. Next, the cells were incubated with primary antibody at 4° C. overnight: Stem cell marker antibody kit (R&D Systems, 1:300), anti-Tra-1-60 (Stemgent, 1:300) and anti-Rex1 (Stemgent, 1:300) were used for pluoripotency markers. For in vitro differentiation, Tuj1 (Covance, 1:500), Nestin (Millipore, Neural Stem cell Characterization Kit, 1:10), MF20 (Development Studies Hybrioloma Bank, Super, 1:300), APF (Thermo Scientific, 1:200), Desmin (Thermo Scientific, 1:300) and Brachyury (Santa Cruz, 1:300) were used. After washing three times in 1% serum PBS for 10 minutes, cells were incubated with secondary antibodies (1:400 in 2% serum PBS) for 2 hours in room temperature: Alexa Fluor 555 donkey anti-goat IgG (1:2000, Invitrogen), Alexa Fluro 488 donkey anti-rabbit IgG (1:2000, Invitrogen) and Alexa Fluro 488 donkey anti-chicken IgG (1:2000, Invitrogen). Nuclei were detected by DAPI using the DAPI cooperated mounting medium (VactorLab). Fluorescence images were taken using an ApoTom (Zeiss) Axl0plan 2 Imaging System.

Teratoma Formation.

The whole dish passaging was used to expand piPSCs for teratoma formation. At passage 3, piPSCs were suspended in DMEM containing 10% FBS. SCID or athymic Balb/c mice (NxGen Biosciences) were anesthetized with diethyl ether and the cell suspension was injected under the kidney capsule and under the muscle. Tumors were clearly visible at the fourth week and were surgically dissected at the sixth week after injection. Tissue samples were fixed in PBS containing 4% formaldehyde, and embedded in paraffin. Sections were stained with hematoxylin and eosin.

DNA Methylation Study.

Genomic DNA was isolated from both HNFs and piPSCs using DNeasy Blood & Tissue Kit (Qiagen, Valencia, Calif.) and fragmented by sonication to shear the DNA into small fragment (400-1000 bp in size). Methylated DNA was isolated from the fragmented genomic DNA via binding to the methyl-CpG binding domain of human BD2 protein using a MethylMiner Methylated DNA Enrichment Kit (Invitrogen) using a protocol suggested by the manufacture. A qRT-PCR was performed using a StepOne Plus Real time PCR system (Applied Biosystems) to determine the Ct value of the Nanog gene promoter region sequence for each of the methylated DNA samples using a pair of primers (Nanog gene promoter region: −1519 to 1498 and −1307 to −1327) for amplifying a 192 bp DNA fragment. As an internal control, the Ct value of the β-actin gene was also determined for each of the methylated DNA samples using a pair of primers (Exon 5) for amplifying a 154 bp DNA fragment. The level of the Nanog gene promoter region DNA in the HNFs was counted as 100% and the level of the Nanog gene promoter region DNA in piPSCs was calculated as fold change relative to that of the HNFs using a StepOne software v2.1 (Applied Biosystems).

SKY Analysis.

Cell cultures and chromosome preparation: Cells were harvested following a 2 hour treatment of Colcemid (0.1

µg/ml). After conventional hypotonic treatment (0.4% KCl, 37° C. for 10 minutes), chromosome preparations were fixed with 3:1 methanol:acetic acid (3×) and the slides were prepared by the air-dry method. Following pepsin treatment and fixation with formaldehyde, slides were subject to dehydration. The chromosomal slides were then denatured in 70% formamide and 2×SSC and hybridized with denatured human painting probes (SKYPaint) for over 48 hours at 37° C. Signals were detected following a series of steps of slide washing. DAP1 staining was also used for visualizing the chromosome/nuclei. 50 mitotic figures with good hybridization quality were randomly captured using CCD camera. Following image acquisition, chromosomes were karyotyped with Applied Spectral Image software.

Results

A Simple piPSC Protocol.

Figure 3:
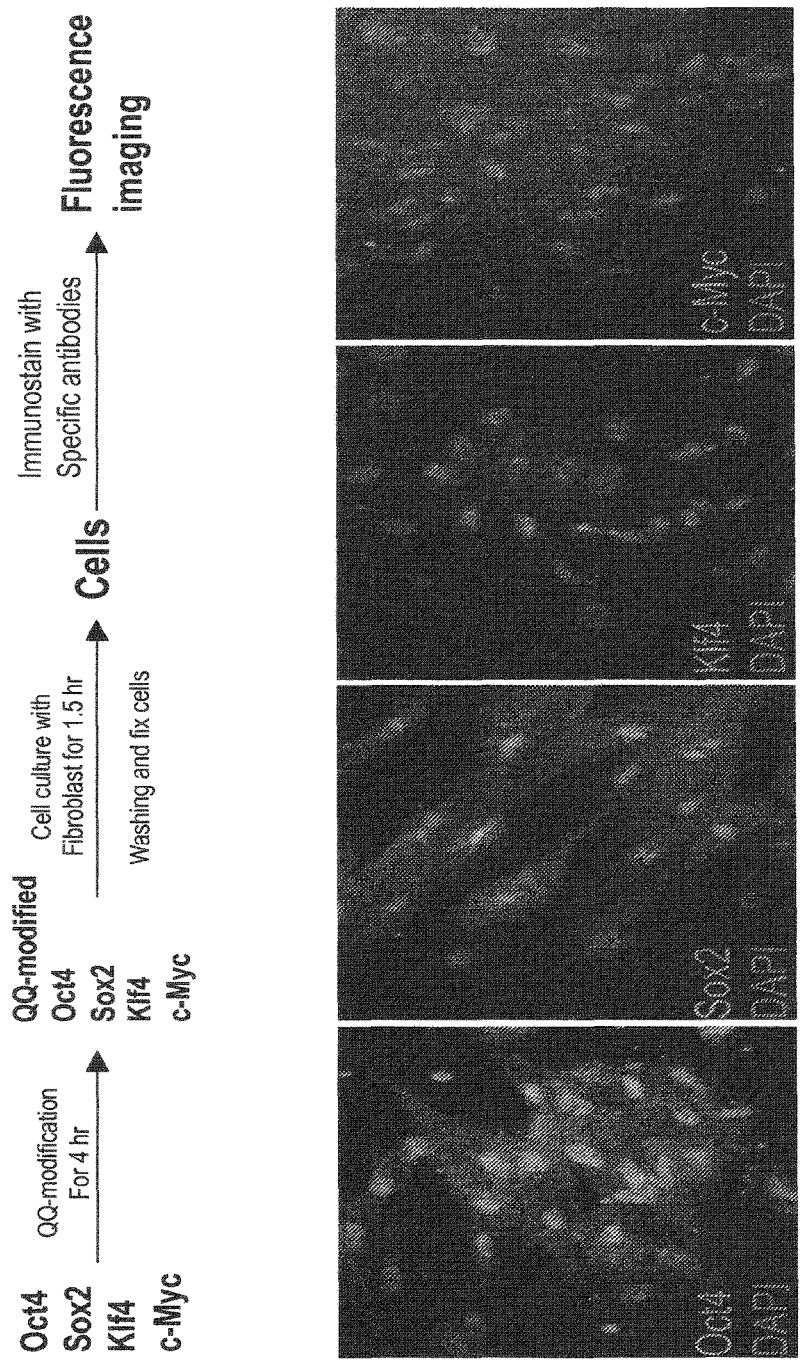
FIG. 3 shows fluorescence images of immunostains of human newborn fibroblast cells after QQ-delivery of reprogramming proteins for 1.5 hr, including Oct4, Sox2, Klf4 and c-Myc, showing nuclear locations of the delivered proteins. The experimental condition is shown in the upper panel. Since the fluorescence images were taken for the fibroblast cells during protein delivery, reprogramming proteins can be observed in both cytosol and nuclei of the cells.

This piPSC technique contains steps of preparation of bacterially expressed reprogramming proteins, QQ-modifications and 1-5 cycles of cell reprogramming, depending on the different starting cells (FIG. 1). An efficient bacterial expression method was reported recently (FIG. 2A), allowing for production of 80-120 mg of pure recombinant proteins for Oct4, Sox2, Klf4 and c-Myc from one-liter of bacterial expression (FIG. 2B). Since the bacterially expressed recombinant proteins may not fold properly, an in vitro protein refolding method was used in the prior piPSC protocol by Zhou et al, which was inefficient and an additional purification step was required. However, an in vivo protein refolding technique was recently developed that directly delivers bacterially expressed recombinant reprogramming proteins into mammalian cells using the QQ-protein delivery, where the intracellular folding machinery efficiently refolds the proteins. The piPSC protocol applies the principle of this in vivo protein refolding technique. The four reprogramming proteins were delivered into the nuclei of HNFs using QQ-protein delivery technique for refolding and function to initiate cell reprogramming (FIG. 3). Each reprogramming cycle is 24 hours: HNFs were incubated with four reprogramming proteins for 3-12 hours, allowing protein delivery into the cells, followed by switching to a regular cell culture medium for 12-21 hours (FIG. 1).

Figure 4:
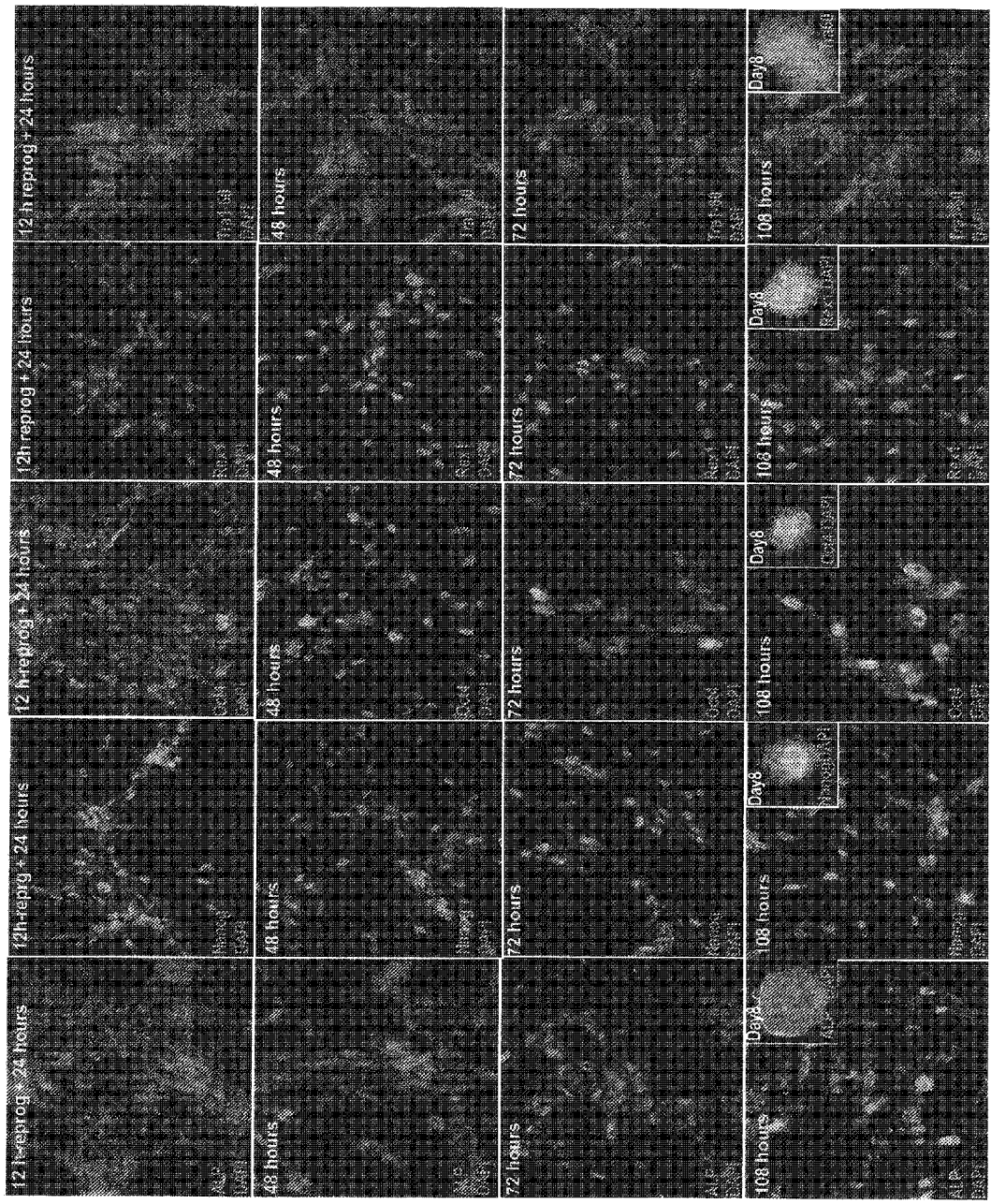
FIG. 4 shows a time-course experiment using immunostains with antibodies against several pluripotency markers. HNF was incubated with the QQ-modified four factors for 12 hrs and then switched to a regular medium for another 108 hours. At 24, 48, 72 and 108 hour, monolayer cells were prepared for immunostaining. Fluorescence signals were observed inside the cells stained with Oct4 at 24 hour in both nuclear and cytosol locations. However, cytosolic Oct4 significantly reduced at 48 hours and only observed in nuclei at 72 hours with reduced fluorescence intensity. At 108 hours, nuclear stains are significantly enhanced again. This data, for the first time, suggests a switch at 72-hour that controls endogenous Oct4 gene expression and degradation of the QQ-delivered exogenous Oct4 inside the nuclei. A constant endogenous Oct4 expression at 108 hour indicate maintenance of cell reprogramming induced by four reprogramming proteins, which is confirmed by immunostains of other pluripotency markers including ALP, Nanog, Rex1 and Tra-160. Clearly, fluorescence signals of these pluripotency markers are observed at 24-hour and become much stronger at the later time points, indicating the endogenous expression of these pluripotency genes are initiated at 24-hour and well-maintained in the later time points. Strong fluorescence stains of Rex1 and TRA1-60 indicate endogenous protein expression of late pluripotent markers, suggesting that protein-induced cell reprogramming is possibly completed in 4-5 days. This result was confirmed by observation of large numbers of colony formation at days 6-8 (Insets).

For protein-induced cell reprogramming, the delivered transcription factors are required to reach the nuclei to initiate cell reprogramming. QQ-delivered reprogramming proteins reached the nuclei of virtually every cell 1.5 hours after delivery (FIG. 3). The delivered proteins were also observed in the cytosol since fluorescence imaging was performed during protein delivery. This result shows that protein-induced cell reprogramming may be initiated within a few hours after protein delivery. It was demonstrated that protein-induced cell reprogramming of HNFs was initiated within the first 24 hours and completed within 5-days, as judged by immunostaining using late pluripotency markers such as Rex1 and Tra1-60 (FIG. 4). This was further confirmed by colony formation in the dishes of cell reprogramming at days 8 (FIG. 4).

Optimizations of the piPSC Protocol.

Protein concentrations were first optimized using the number of alkaline phosphatase (ALP) positive colonies as the criteria for optimization. The data indicated low conversion efficiency with a high concentration of reprogramming proteins. When a 5 µg/ml protein concentration was used, only a few ALP-positive colonies were found. A lower concentration generated more ALP-positive colonies, with a concentration of reprogramming proteins at 0.25-0.50 µg/ml generating the most ALP-positive colonies in 5 days (Table 1). This result is supported by the published data of human embryonic stem cells (hESCs), indicating that the concentration of Oct4 inside ESCs is critical, because a higher Oct4 concentration causes ES cell differentiation, whereas a lower Oct4 concentration fails to maintain pluripotency. In addition, c-Myc is oncogenic protein that may cause higher rates of mutations and participate in tumorigenesis at high intracellular concentrations. An optimized concentration of four reprogramming proteins is critical to the quality of the generated piPS cells. The QQ-protein delivery permits us to control the concentration of the delivered proteins inside the nuclei of HNFs (Table 1), allowing quick optimizations of protein concentrations.

Optimizations of the Cell Reprogramming Protocol were Also Performed.

The initial protocol (3-hour reprogramming) was repeated with only one cycle of reprogramming and the cells were immunostained using the anti-ALP antibody at the end of the cycle. Only ~30% of HNFs showed strong ALP staining (FIG. 5D). As a control, HNF cultured with a regular culture medium without reprogramming proteins for 24 hours showed no ALP staining (FIG. 5C). When a 5-hour reprogramming was performed, significantly more cells (~0.60%) showed strong ALP staining (FIG. 5E). A 24 hour continue culture of HNFs with four reprogramming proteins (0.1 µg/ml) indicated that virtually every HNF cell was ALP-positive (FIG. 5F), suggesting possible very high conversion efficiency of cell reprogramming. This data provide direct evidence of the enabling capability of the QQ-protein delivery in protein-induced cell reprogramming.

The optimized piPSC protocol usually delivered Oct4/Sox2/Klf4/c-Myc at a 1:1:1:0.1 ratio with a protein concentration of 0.5 µg/ml for Oct4 for the first cycle and reduced protein concentration by half in the cycle thereafter. 1-5 cycles of reprogramming were usually performed, depending on the starting human somatic cells. For HNF, 2-3 cycles of reprogramming was enough to generate piPS cells. At the end of reprogramming, the culture medium was switched to a feeder-free maintaining medium containing FGF (10 ng/ml) for 2 days. The cells were lifted up and transferred into new dishes, which were pre-treated with the conditioned medium for 10 minutes. The cells were cultured with half conditioned medium and half new feeder-free maintaining medium. At day 5-6, many clear edged colonies were observed (FIGS. 5A and 5B). The entire dish contains 500-1500 piPSC colonies from $10^5$ starting cells. In a recent study using protein extracts from mouse ES cells, similar piPS-like cells were also made in 5 days but with much lower efficiency.

High Conversion Efficiency.

This piPSC technique gives high conversion efficiency of piPSCs from human somatic cells. Many colonies were usually obtained in the first or second passage. In FIG. 6A, the left panel shows many colonies in a dish. The colonies were stained with a red ALP kit; the right panel shows the zoomed-in image of the boxed area, displaying red ALP-stained piPSC colonies. To assess conversion efficiency, monolayer piPSCs were intentionally prepared from colonies and immunostaining was performed with monolayer cells using ALP, SSEA4, Nanog, Oct4, Rex1 and Sox2 antibodies (FIG. 6B). Immunostaining was also performed on the starting HNFs, showing negative stains (FIG. 6B). To estimate conversion efficiency, a minimum of 10 randomly selected fields was scored for positively and negatively stained cells (>400 cells) in a double-blinded manner to minimize subjective interpretations after fluorescence imaging. The conversion efficiency was then calculated by the ratio of positively stained cells/total counted cells. In FIG. 6C, the right panel shows the results, indicating that the average reprogramming efficiency is between 80-91%. This result is consistent with the previous time course, suggesting that this piPSC technology can generate piPSCs with an average of 85±4% conversion efficiency. In a previous time course experiment, there was also demonstrated an average of 88±2% conversion efficiency with a similar cell reprogramming protocol that used the QQ-protein-delivery (Table 2).

Figure 7:
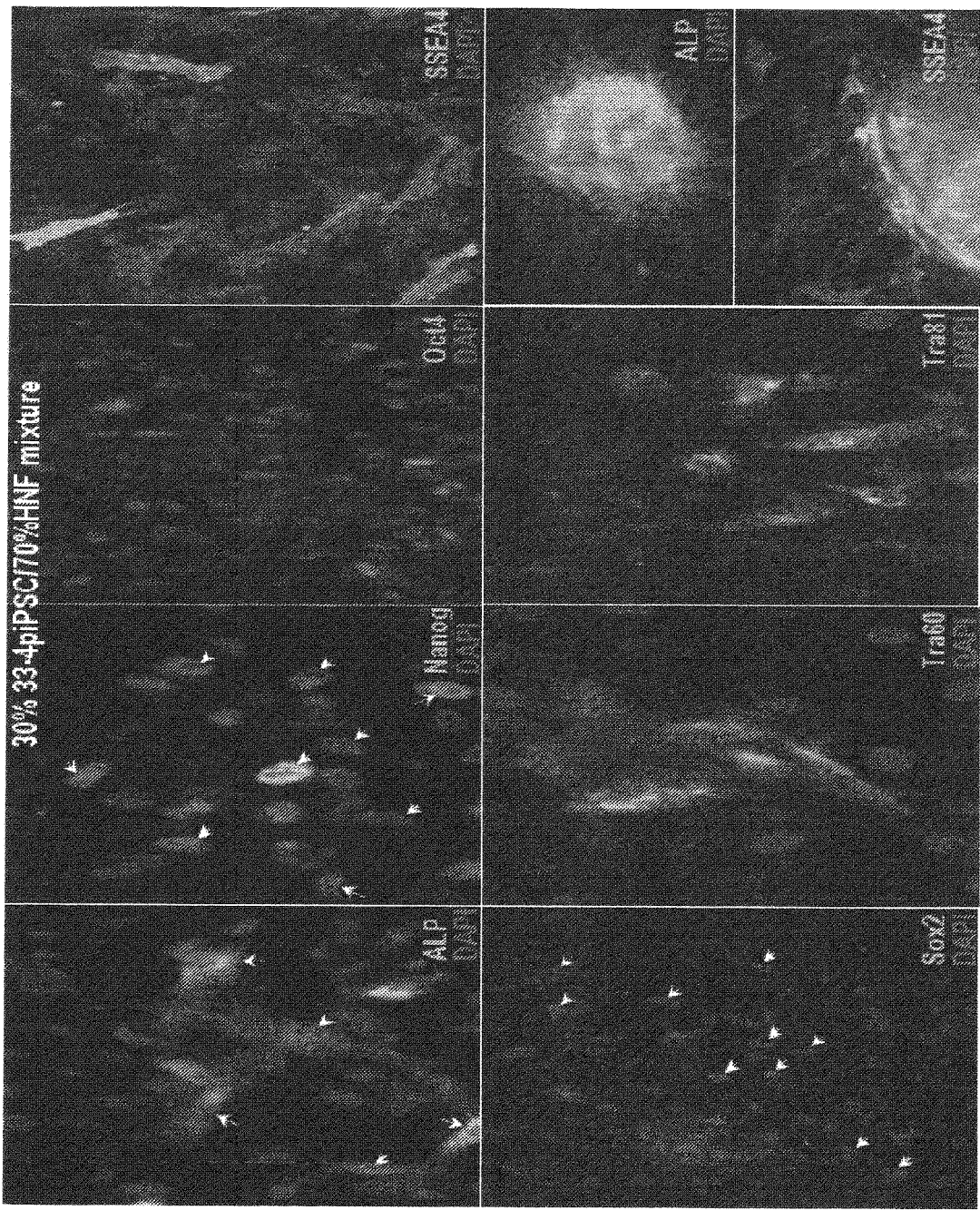
FIG. 7 shows Fluorescence images of an internal control experiment for immunostains using six pluripotency markers (as labeled) to a cell mixture of 30% piPSCs ($4^{th}$ passage) and 70% HNFs, showing the expected dilution of the positively stained cells. Lower Right: Fluorescence images of two colonies with monolayer cells, showing both the colonies and monolayer cells are positively stained for ALP and SSEA4.

To confirm this result, double immunostaining was performed using three pairs of pluripotency markers: SSEA4/Oct4, Tra1-60/Nanog and Tra1-60/Oct4 (surface/nuclear markers). In FIG. 6B, the right panel displays examples of these double stains with Oct4/Nanog in red, Tra1-60 in green and DAPI in blue. The positive piPSCs were considered only when both nuclei and surface markers showed positive stains. Once again, the results confirmed ~80% conversion efficiency (FIG. 6B, Right Panel). To further verify that the immunostaining is truly positive, an internal control experiment was performed using six pluripotency markers to a cell mixture that contains 30% piPSCs and 70% starting HNFs. The data indicated the expected dilution of the positively stained cells (FIG. 7), providing additional support to the high conversion efficiency.

Such high conversion efficiency suggests that colony selection may not be necessary during cell reprogramming to generate piPS cells and clonal expansion may not be required during piPSC expansion. A recent report indicated that long-term culture of human ESCs under a similar feeder-free condition only contained a population of 85-94%) hESCs by flow cytometry using different pluripotency markers. This result is similar to the conversion efficiency reported here, suggesting that the piPSC method generates a nearly pure population of piPSCs.

Figure 8:
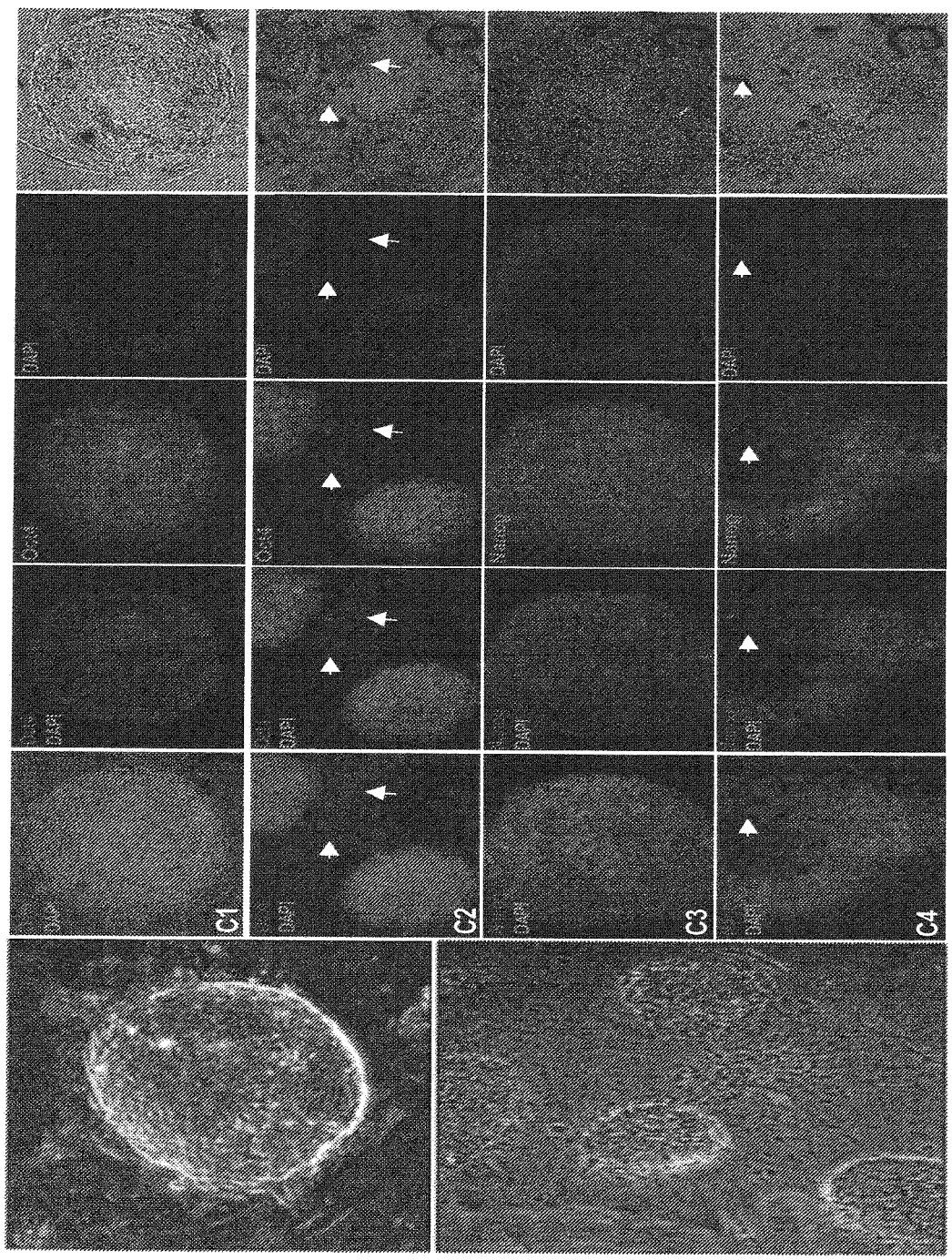
FIG. 8 shows characterization of pluripotency of the generated piPS cells using a single colony passaging approach. Briefly, after completion of cell reprogramming, a single colony with a clear edge (A) was chosen and passaged for three more generations using the feeder-free condition. It was noticed that this single colony started to lose the clear edge in several days after passaging and the cells scrolled out of the colony during cell proliferation. Once the cell reached confluency, the cells were lifted and passaged into a new dish, many clear edged colonies formed at the second day. However, the cells repeated the above process during their proliferation. There were observed cells scrolled out of the colonies (green arrow), while other colonies maintain a clear edge (white arrows) (B). Using the same piuripotent markers, immunostains were performed to both clear edged colonies (C1 and C3) and monolayer cells that scrolled out of the colonies (02 and 04) for Oct4 and Nanog as examples. It is evidenced that both types of cells were positive, suggesting that they are piPSC-like cells. We also passaged the whole dish cells without pick any colonies for three generation. We then compared the cells with both single colony passage and whole dish monolayer cell passaging and observed no difference in the immunostaining using six piuripotent stem cell markers.

Experiments shown in FIG. 8 were performed with both colony picking and whole dish passaging. First, a single clear edged colony was picked and placed into the feeder-free condition. It was noticed that this single colony started to lose its clear edge over several days and the cells spread out into a monolayer. This was also noticed by Rodin et al that pure hESCs spread out into a monolayer when plated in small clumps under a similar feeder-free condition. Once the cells reached confluency, they were lifted and passaged into new dishes. Many clear edged colonies formed next day and piPSCs often migrated out of the colonies (green arrow), while some colonies maintained a clear edge (white arrows). These migrating cells form monolayer cells that may serve as the feeder cells for the remaining colonies. Immunostaining of both clear edged colonies and monolayer cells was performed using Oct4 and Nanog antibodies. The data clearly indicated that both types of cells were positively stained, suggesting that both colony and monolayer cells are piPSCs. The same procedure was repeated with the whole dish passaging and the same results were observed. For the whole dish passaging, data indicated that 80-90% of cells had positive immunostains with six pluripotency markers (FIG. 6C), suggesting no difference between the two passaging methods under these conditions.

Characterizations of piPSCs.

Figure 9:
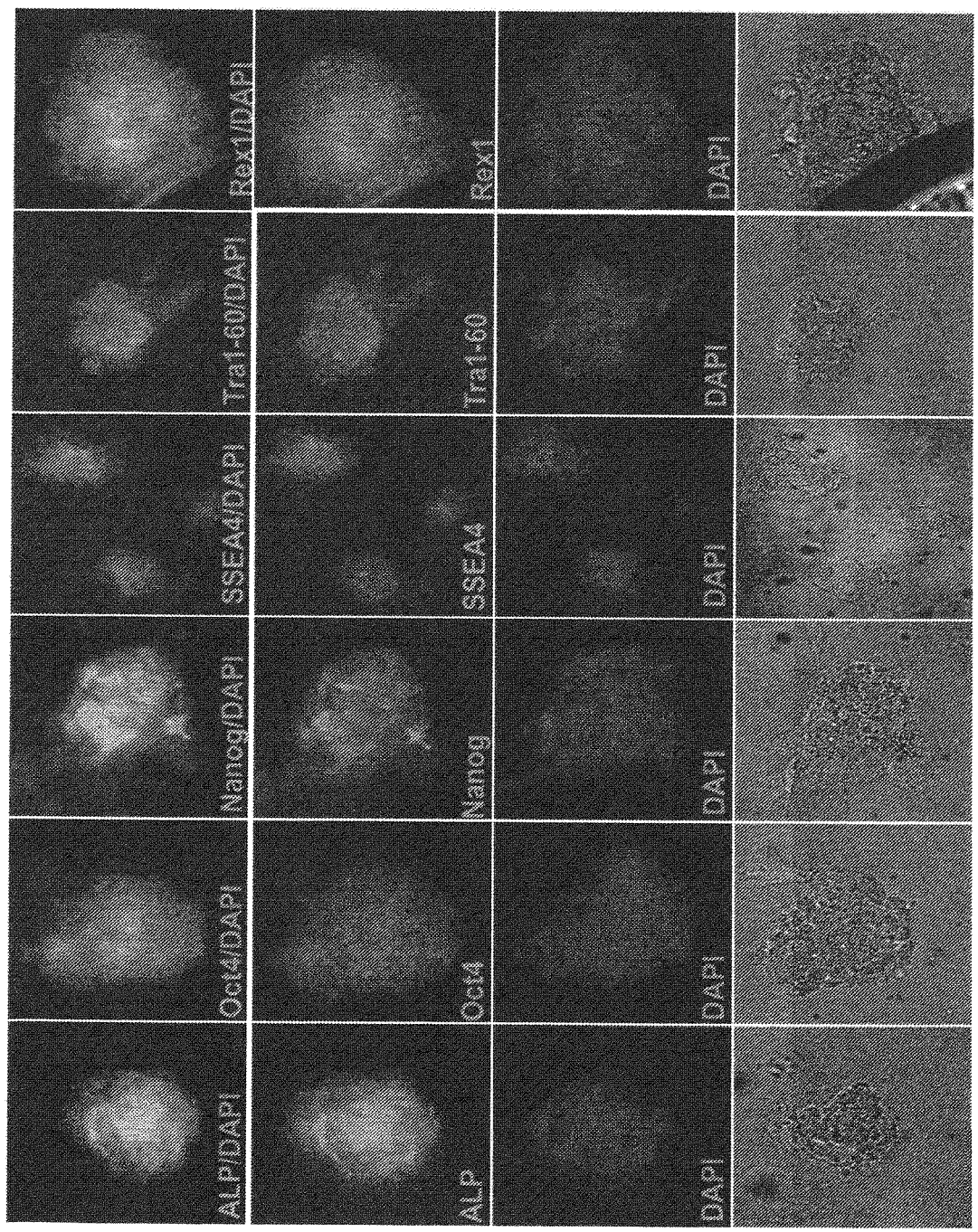
FIG. 9 shows fluorescence images of immunostains of the piPSC colonies of the $30^{th}$ passage of #19 reprogramming (6.5 months, using the whole dish monolayer cell passaging method) under our feeder-free culture condition using ALP, Oct4, Nanog, SSEA4, Tra1-60 and Rex1. Nuclei were labeled with DAPI.
Figure 10:
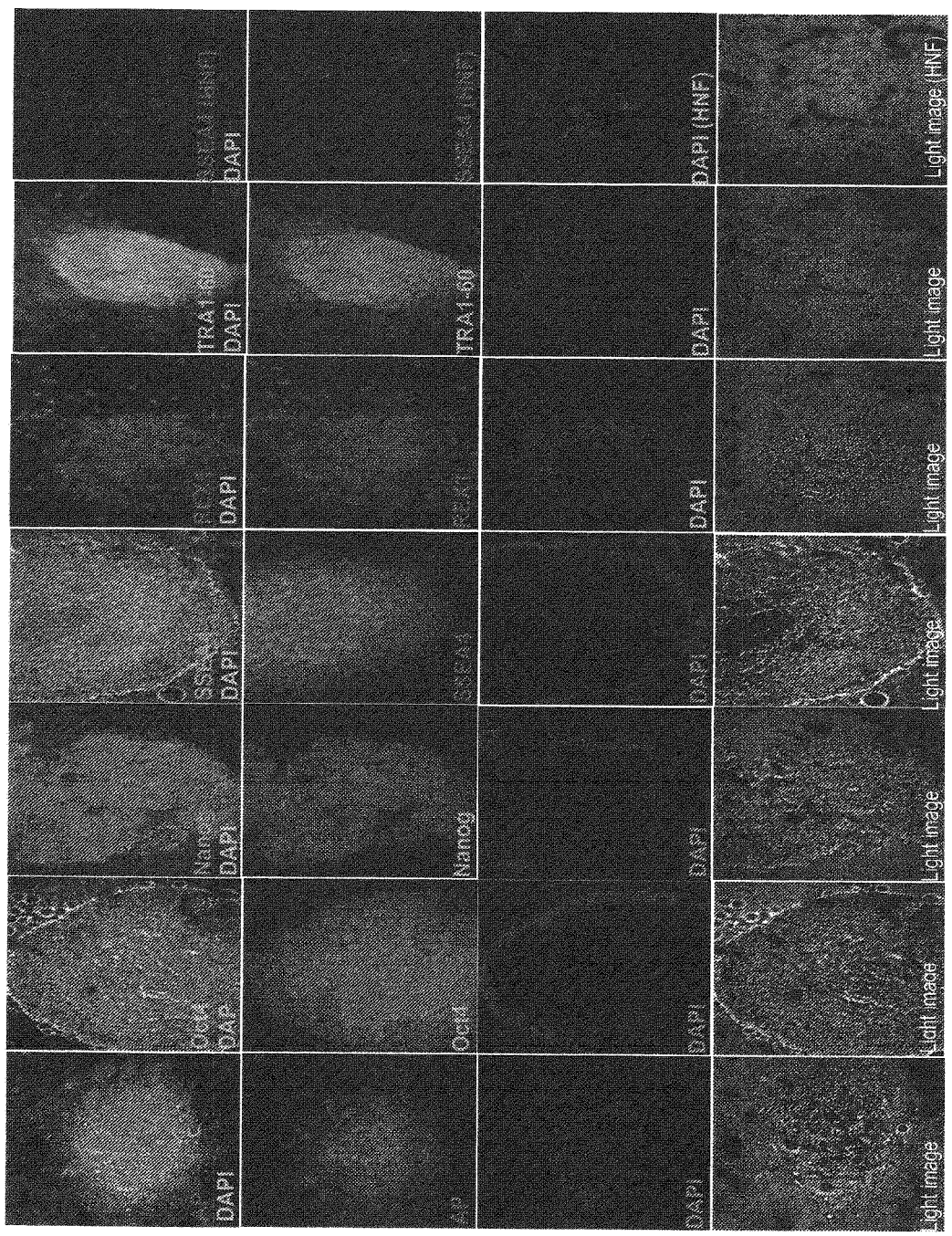
FIG. 10 shows fluorescence images of immunostains of the piPSC colonies from the $19^{th}$ cell reprogramming at the $6^{th}$ passage (50 days) using a whole dish passaging approach under our feeder-free piPSC culture condition. Briefly, the whole dish was passaged by lifting-up the cells in the whole dish and passaging into two dishes without picking up a single colony. The passaged dishes formed hundreds of colonies next day. At 6 passage, these piPS cells were characterized, including both piPSC colonies and monolayer cells, using immunostains. Six pluripotent markers, including ALP (early marker), Oct4, Nanog, SSEA4 (intermediate marker), Rex1 and Tra1-60 (late markers), were used. A negative control is also shown with SSEA4 antibody using HNF. The HNFs show only individual cells without colony formation. This figure shows that the generated piPSC colonies stained positive for all six pluripotency markers, suggesting that the generated piPSC colonies are pluripotent stem cells.
Figures 11A, 11C, 11D:
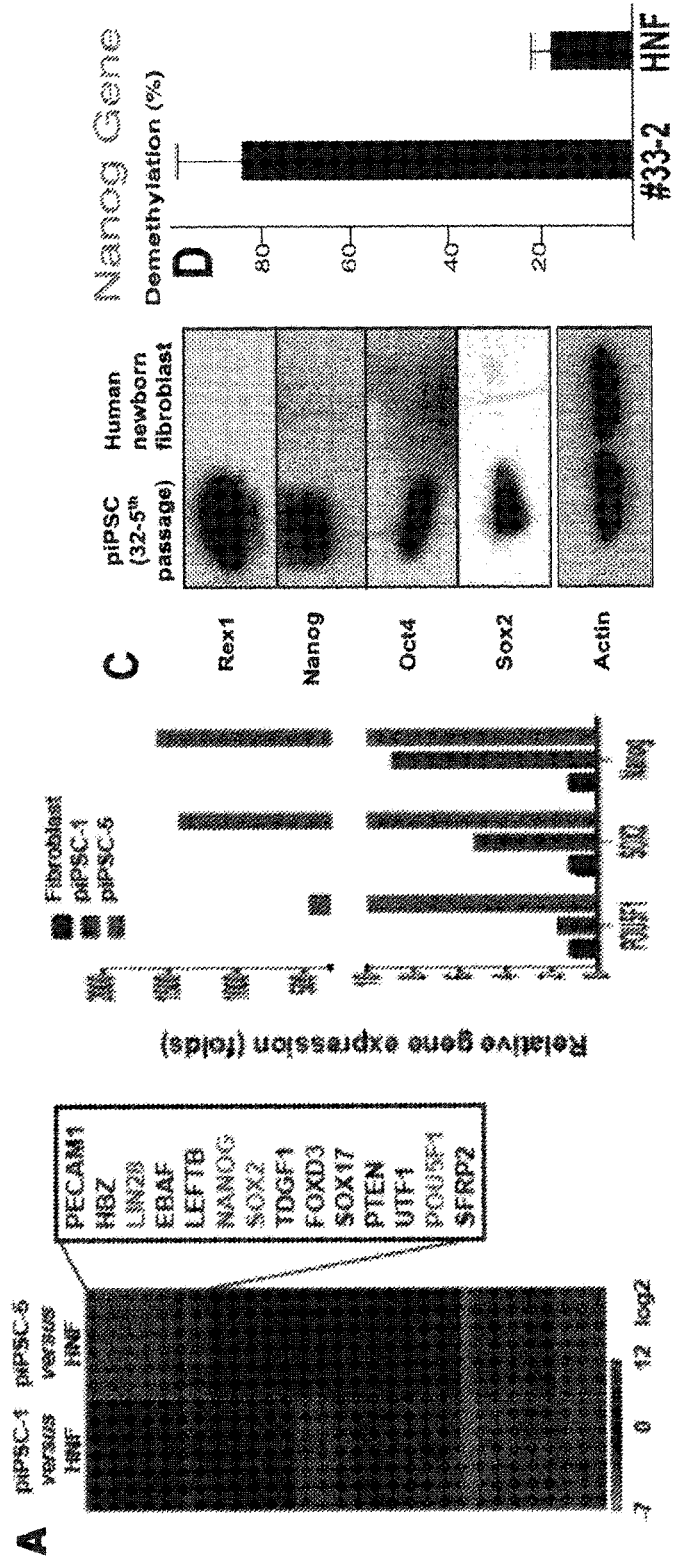
FIGS. 11A-11D show characterizations of piPS cells expanded using the whole dish monolayer cell passaging method.
Figure 11B:
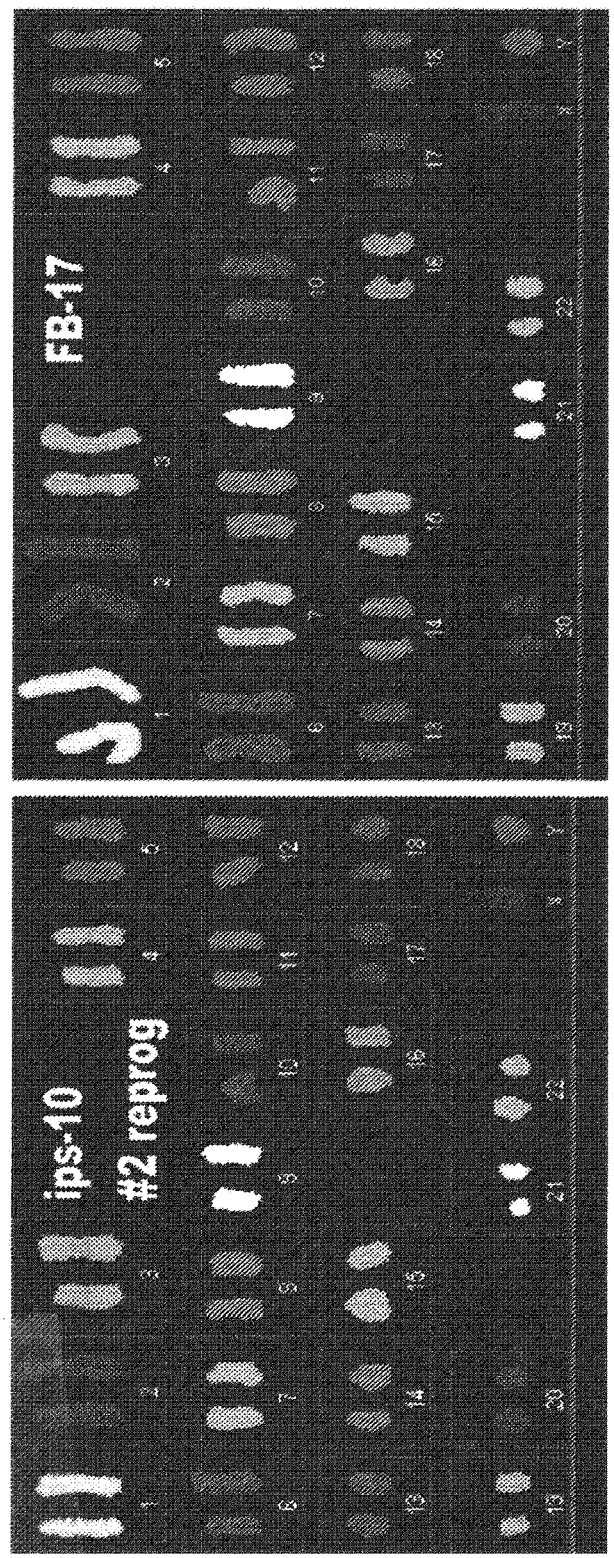

Using the whole-dish passaging, the generated human piPSCs have been stably and homogenously expanded for over 30 generations in a feeder-free culture condition for 6 months (FIG. 9). They formed colonies with the morphology that is indistinguishable from hESCs. These piPSC colonies prominently expressed ESC markers, including ALP, Oct4, Nanog, SSEA4, Rex1 and Tra1-60 (FIG. 10). As controls, the same immunostaining was performed using the starting HNFs, showing negative results (Right, FIG. 10). Quantitative reverse transcription PGR (qRT-PCR) analysis confirmed significantly enhanced endogenous gene expressions of pluripotency genes in piPSCs at passage 5, including: Oct4, Sox2, Nanog, as compared with gene expression of HNFs (FIG. 11 A). It is noticed that the gene expression of these master pluripotency regulators displayed a minor enhancement at the first passage (Day 6), but a major enhancement at passage 5 (day 22), indicating the time-dependence of the pluripotency development after cell-reprogramming. To verify pluripotency protein expression, western blots of the piPSCs were performed and compared with the starting HNF cells. The results indicated significant protein expressions of the piPSCs for four pluripotency markers, including Sox2, Oct4, Nanog and Rex1. Sox2, Oct4 and Nanog are the three master pluripotent regulators and Rex-1 is a late pluripotency marker. In contrast, the starting HNF cells displayed no protein expressions of these four pluripotency markers. As a control, a housekeeping protein, actin, displayed an equal protein expression level between piPSCs and HNFs (FIG. 11C). DNA methylation analysis of the Nanog gene revealed that the promoter regions of Nanog were significantly demethyiated in the piPSCs, whereas the same regions were densely methylated in the parental HNF cells (FIG. 11D). This result provides further evidence that the generated piPSCs display an epigenetic regulation of the promoters of this master pluripotency regulator, suggesting appropriate epigenetic cell reprogramming in the generated piPSCs. There was no karyotype change between the generated piPSCs and the parental HNFs (FIG. 11B), indicating no major chromosomal change between the parental HNFs and the daughter piPSCs.

In Vitro and In Vivo Differentiations.

Figures 12A, 12B, 12C:
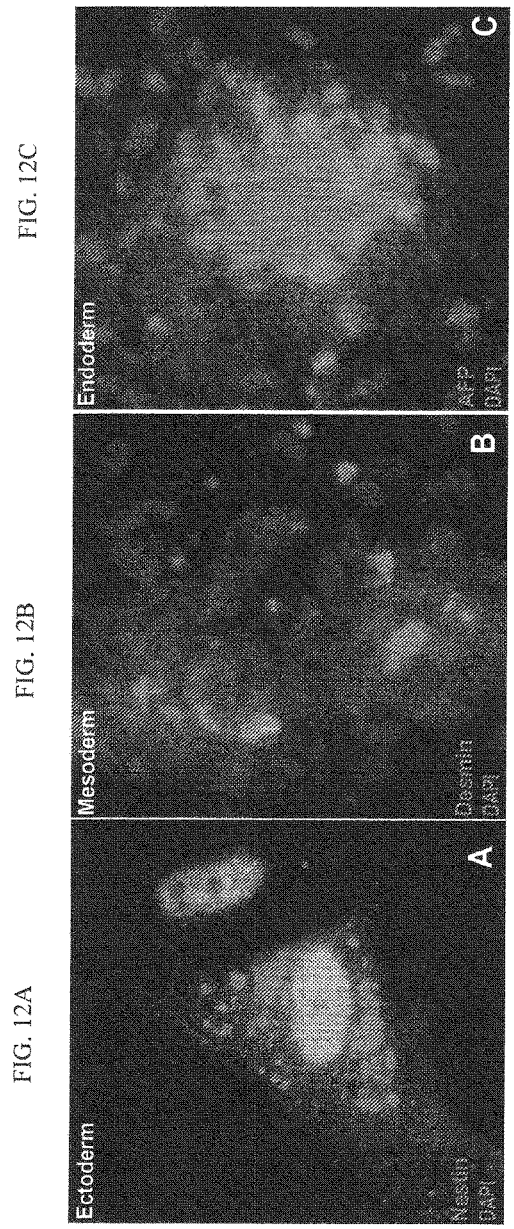
FIGS. 12A-12C show differentiation capability of the piPS cells expanded using the whole dish passaging method. Upper: In vitro spontaneous differentiation of piPSCs. Immunostaining images show all three germ layer cells at day 14; neural.
Figures 12D, 12E, 12F, 12G, 12H, 12I:
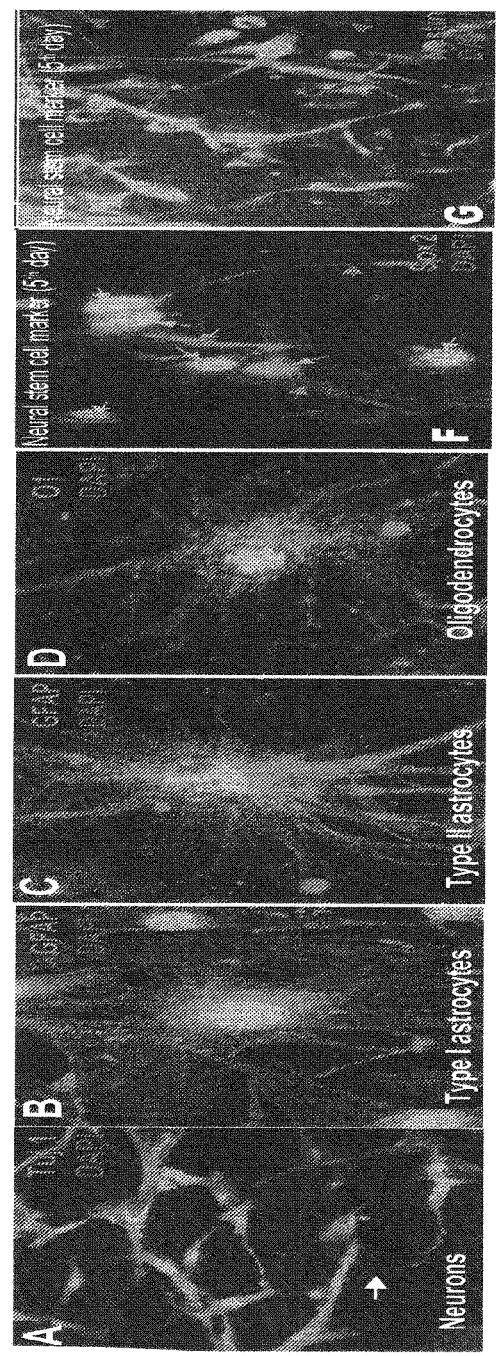
FIGS. 12D-12I shows fluorescence images of in vitro specific differentiations of piPSCs to neural lineages.

To examine the developmental potential of the generated piPSCs, in vitro differentiation and in vivo teratoma formation were performed. Embryoid bodies (EBs) were formed in 1-2 days using the suspension culture method. These EBs readily differentiated into the three primary germ layers in vitro, including ectoderm derivatives (cells expressing Nastin and Pax6), mesoderm derivatives (cells expressing Desmin and Brachyury and mature beating cardiomyocytes) and endoderm derivatives (cells expressing AFP), as confirmed by immunostaining (FIGS. 12A-12C). Proper negative controls have been performed for immunostaining using the parenting HNFs, showing negative immunostains. When the EBs were cultured in a special medium that leads to neural lineage, these EBs readily changed their morphologies in 1-2 weeks into the typical morphology of neural cells, including neurons, astrocytes and oligodendrocytes, immunocytochemical analysis confirmed the existence of these neural cell types positive for Tuj1 (FIG. 12D), GFAP (FIGS. 12E-12F) and OI (FIG. 12G). Neural stem cells (NSCs) were also observed at an earlier time as confirmed by positive stains with Sox2 (FIG. 12H) and Nestin (FIG. 12I).

Figures 13A, 13B:
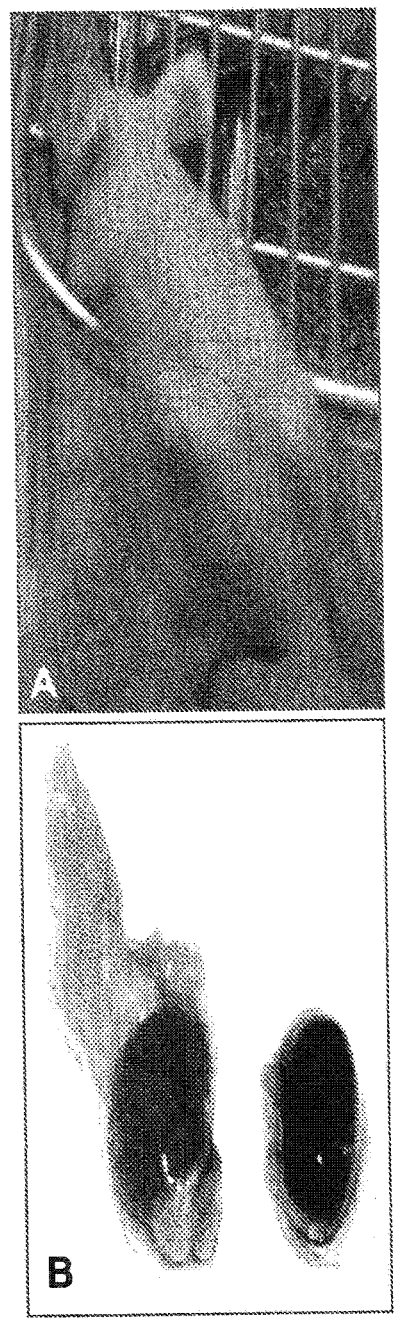
FIG. 13A shows Teratoma formation (1). The whole dish passaging method was used to generate enough piPSCs for teratoma formation. At passage 3 (25-day), piPSCs were suspended in DME containing 10% FBS. SCID (NxGen Biosciences) mice were anesthetized with diethyl ether and the cell suspension was injected under the kidney capsule and under the muscle. Tumors were clearly visible at the fourth week and were surgically dissected at the sixth week.
FIG. 13B shows the piPSC-injected kidney was compared with the kidney without injection, clearly showing enlargement of the piPSC-injected kidney.
Figure 13C:
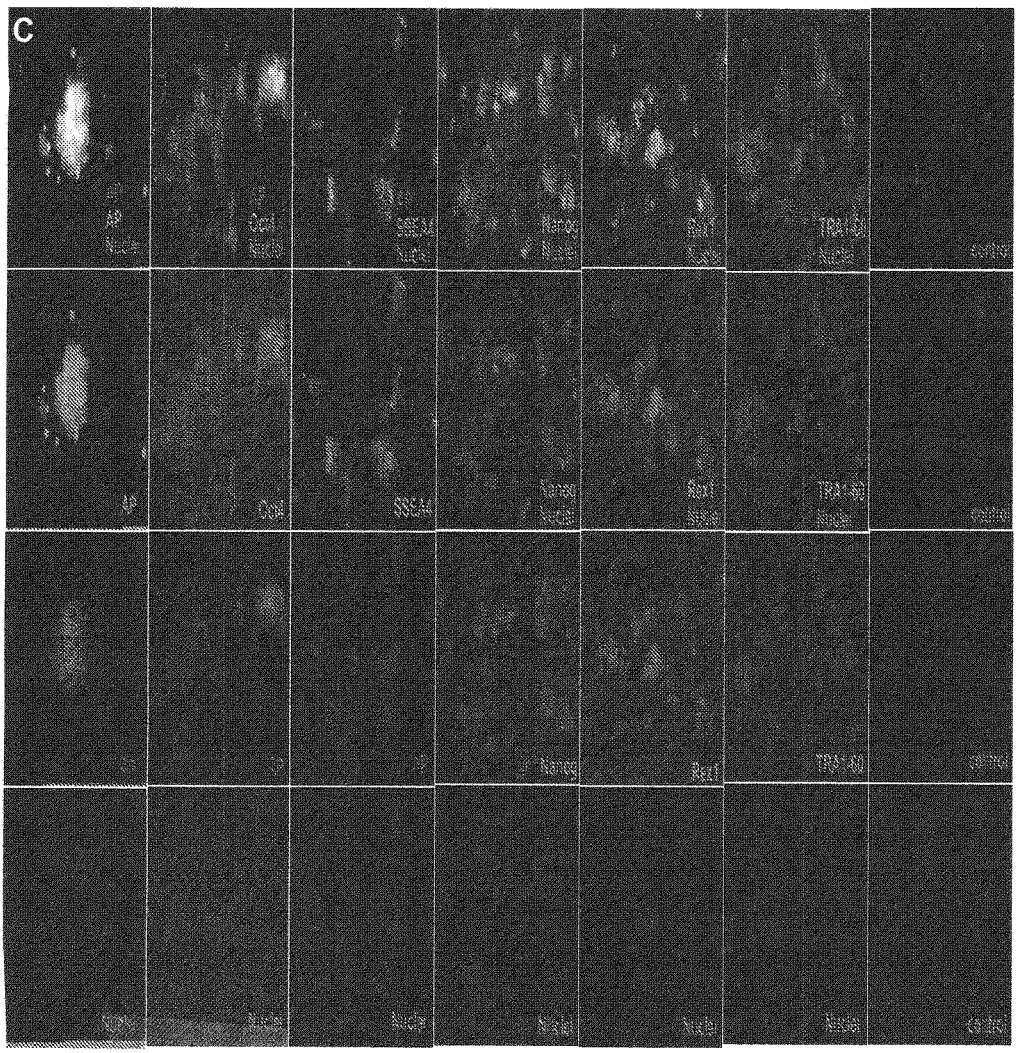
FIG. 13C shows fluorescence images of immunostains of the piPS colonies and monolayer cells used for teratoma formation with a whole dish passaging method. A negative control of the same immunostain with SSEA4 using the starting HNF was also showed (Right). The piPSC colonies were broken into monolayer cells and then performed immunostains. The results indicated that virtually every cell displayed positive stains for all six pluripotency markers, suggesting a high conversion efficiency using whole dish passaging method. Only 200,000 piPS cells were transplanted into the kidney capsule of nude mice.

When piPSCs were transplanted into the kidney capsule of nude mice, teratoma formation was observed in 6 weeks (FIGS. 13A-13B). The third passage piPSCs obtained from whole dish passaging were used for transplantation. Before transplantation, these piPSCs were characterized using immunostaining with six pluripotency markers. Again, monolayer piPSCs were intentionally prepared for immunostaining (FIG. 13C). The results indicated that virtually every cell displayed positive stains for all six pluripotency markers. Approximately 200,000 piPSCs were transplanted into the left kidney capsule of nude mice. Node-like formations were observed in the left flank area of the mice at three to four weeks following implantation. The mice were sacrificed at six week. Histology data of the tissue slides indicated these teratoma containing tissues form all three primary germ layers, including neural and epidermal tissues (ectoderm), striated muscle and cartilage (mesoderm), and intestinal-like epithelium tissues (endoderm) (FIG. 14), confirming that the generated piPSCs exhibit pluripotency in vivo. This result further provides an in vivo verification of the high conversion efficiency, since the generated piPSCs expanded with the whole dish passaging were able to efficiently generate teratomas.

Recently, the Yamanaka's four reprogramming factors were replaced with Sox2, Oct4 and Nanog which are the master regulators of pluripotency to generate piPS cells. Our data again indicated very high conversion efficiency of 87±3% (Table 3). This new reprogramming protein cocktail eliminates the oncogenic proteins, Klf4 and c-Myc in the Yamanaka's factors, the generated piPS cells will have higher quality and minimized tumorigenesis.

Discussion

The piPSC protocol disclosed herein applied the state-of-the-art QQ-protein delivery technology that solved the technical challenges associated with the current iPSC techniques. First, the QQ-reagents non-covalently bind to the delivered proteins and camouflage them from intracellular protease degradation, ensuring the delivered proteins maintain their native form and metabolic stability. Most importantly, the QQ-delivered proteins have the ability to specifically localize in the targeted intracellular compartments based on their sequence localization signals. These features enable the delivered proteins to be indistinguishable from the endogenous proteins, the cell machinery functions as if they were the endogenous counterparts, demonstrating the physiological relevance of the QQ-protein delivery technology.

Using QQ-protein delivery, the bacterially expressed recombinant reprogramming proteins were directly delivered into the nuclei of HNFs in 1.5 hour (FIG. 3), allowing one to skip the inefficient in vitro protein refolding step. The intracellular protein folding machinery directly refolds the QQ-delivered reprogramming proteins, making this piPSC protocol a fast, simple and inexpensive procedure. The QQ-protein delivery is able to efficiently deliver four reprogramming proteins into the nucleus of essentially every HNF, suggesting possible high conversion efficiency of generating piPSCs from HNFs. Data further indicated that cell reprogramming could be initiated within 24 hours of QQ-protein delivery and was well-maintained during 48-72 hours and completed in 5 days after QQ-protein delivery (FIG. 4). This significantly speeds up the procedure of piPSC generation, demonstrating the enabling capability of the QQ-protein delivery technique.

To generate piPSCs with high conversion efficiency, both development gene silencing and pluripotent gene activation of human somatic cells have to be efficiently achieved. This requires efficient delivery of the reprogramming proteins into the nuclei for interaction with different promoter and repressor regions of different genes. The QQ-protein delivery meets this requirement and targeted delivers reprogramming proteins into the nucleus of nearly every HNF, resulting in an 85±4% conversion efficiency of piPSCs from the starting HNFs. This generates a nearly pure piPSC population that is similar to a pure hESC population during long-term self-renewal of hESCs under the similar feeder-free condition. Such high conversion efficiency eliminates colony selection during cell reprogramming and clonal expansion. A whole dish passaging was developed, generating a uniform monolayer piPSC population that is critical to reduce differentiation during long-term self-renewal. Use of homogeneous monolayer piPSCs also provides more controllable conditions for design of differentiation condition, having the major advantage of driving differentiation into more homogenous population of the special lineage cells when they are placed in a special lineage-inducing medium.

Figure 14:
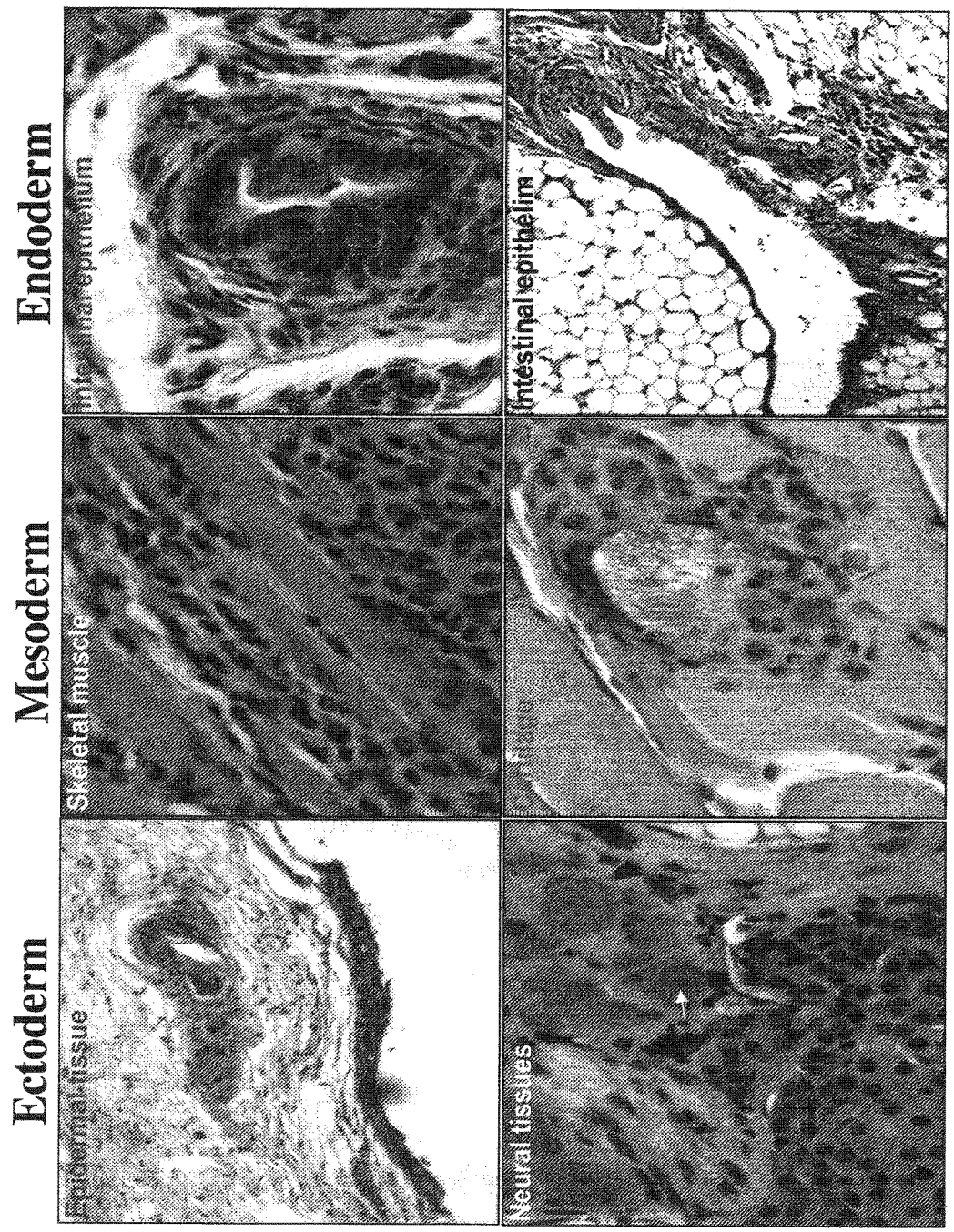
FIG. 14 shows Teratoma formation (2). At the sixth week, the animals were surgically dissected. The kidney tissue samples were fixed in PBS containing 4% formaldehyde, and embedded in paraffin. Sections were stained with hematoxylin and eosin (H & E). H & E staining were performed for teratoma formation derived from piPS cells. Teratomas were well developed from a single injection site after cells were transplanted under the kidney capsules of SCiD mice. The resulting teratomas contained various tissues representing ectoderm, mesoderm and endoderm differentiation. Histology data of the tissue slides indicated these teratoma contained tissues from all three primary germ layers, including neural tissues and epidermal tissues (ectoderm), striated muscle and cartilage (mesoderm), and intestinal-like epithelium tissues (endoderm), confirming that the generated piPS cells using whole dish passaging exhibit pluripotency in vivo.

The generated piPSCs were human ESC-like cells, displaying significantly enhanced expressions of the pluripotency genes, including three master pluripotency regulators Sox2, Oct4 and Nanog (FIG. 11A). These three master pluripotency regulators also displayed major protein expressions (FIG. 11C). The generated piPSCs displayed differentiation potential into the three primary germ layers both in vitro and in vivo (FIGS. 12 and 14). Indeed, these piPSCs were able to efficiently differentiate into neural lineage with typical morphology of neurons, astrocytes and oligodendrocytes (FIGS. 12D-12I). Jaenisch's lab recently demonstrated that reprogramming by four transcription factors was a continuous stochastic process where almost all mouse donor cells eventually gave rise to iPSCs upon continued growth and transcription factor expression. However, this method required 8 weeks to generate iPSCs with inhibition of the p53/p21 pathway or overexpression of Lin28. The piPSC technique disclosed herein confirmed the high conversion efficiency without manipulating any downstream pathways. This has the major advantages for future safe human clinical applications of the generated piPSCs.

Recent advances in using various genetic approaches have addressed some of the challenges of the current iPSC technology. This includes non-integrating adenoviruses, transient transfection to deliver reprogramming genes, a piggyBac transposition system, Cre-excisable viruses and oriP/EBNA1-based episomal expression system. Studies also demonstrate that the present invention can replace and/or further reduce the number of transcriptional factors required for cell reprogramming. Nevertheless, these methods only provide low conversion efficiency and also genetically alter the cells, imposing major biosafety issues of the generated iPSCs for safe human clinical applications. Currently, only two reports are published on protein-induced cell reprogramming for both mouse and human cells with extremely low conversion efficiency. The piPSC technology disclosed herein offers an efficient and fast method to generate human piPSCs. This technology directly delivers bacterially expressed proteins for cell reprogramming, making this method simple and inexpensive. The non-stochastic nature of this piPSC technique makes it possible for reliable and accurate mechanistic studies of cell reprogramming. Importantly, this piPSC technique significantly speeds up the entire process of generating patient-specific piPSCs with high efficiency, allowing one to quickly generate a panel of disease-specific piPSCs as the starting materials for generating surrogate models of human diseases for individual patient, to gain valuable insights into the pathophysiology of the diseases, to discover new prognostic biomarkers and to ensure a continuous supply of afflicted cell types for drug screens and discovery.

Figure 15:
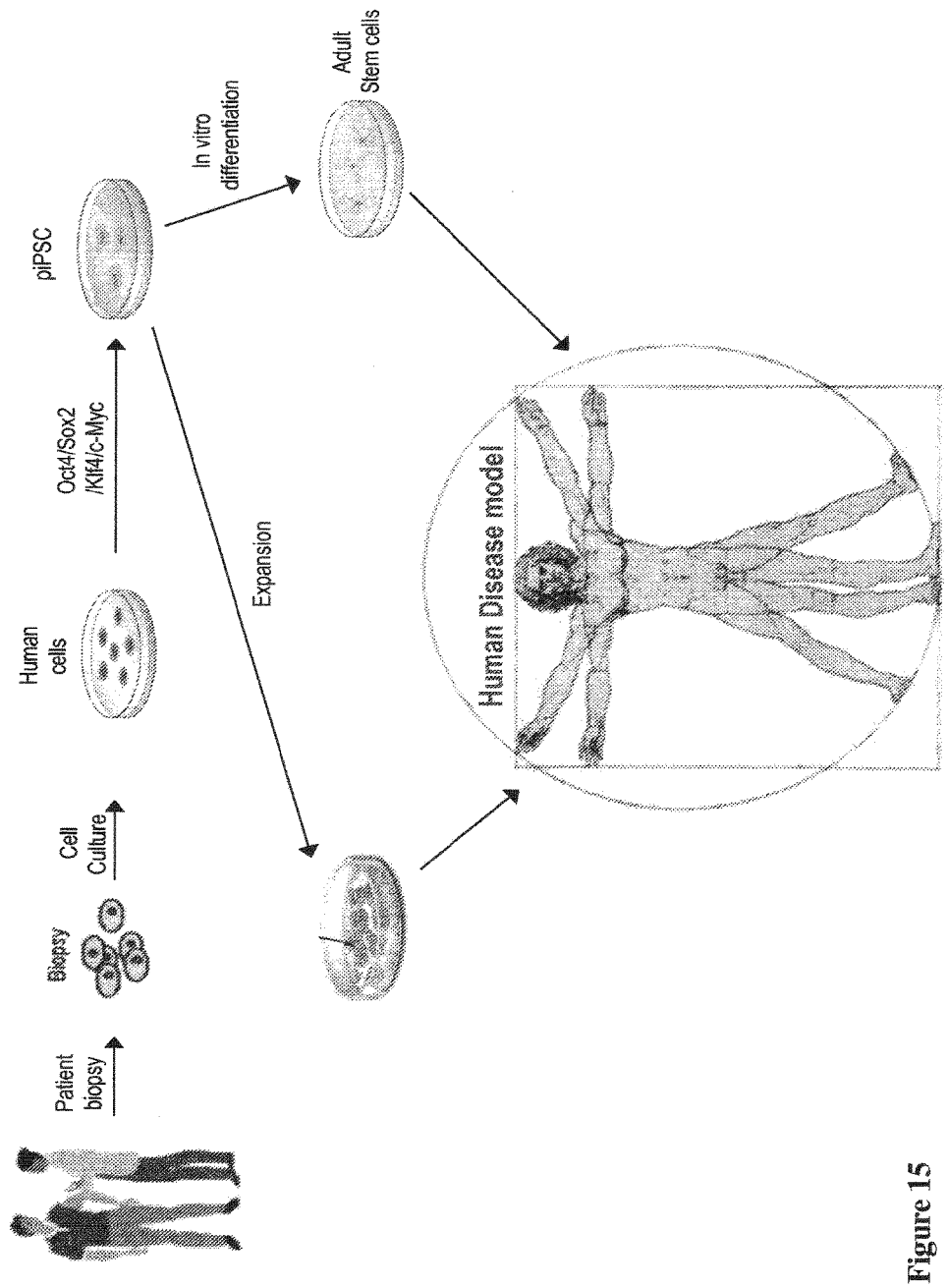
FIG. 15 shows the piPS cells derived from individual patient can be used to generate disease model for that patient. Briefly, primary dermal fibroblasts can be obtained from a patient via skin biopsy and these fibroblasts can be used to generate piPS cells by delivery of four reprogramming proteins. The generated piPS cells can be either expanded or led to specific lineage of adult stem cells, which can be further differentiated into diseased tissues. Thus, these cells can be used to generate disease model since they are generated from an individual patient with a specific disease. Thus, one can study this specific disease in a dish for this individual patient.
Figure 16:
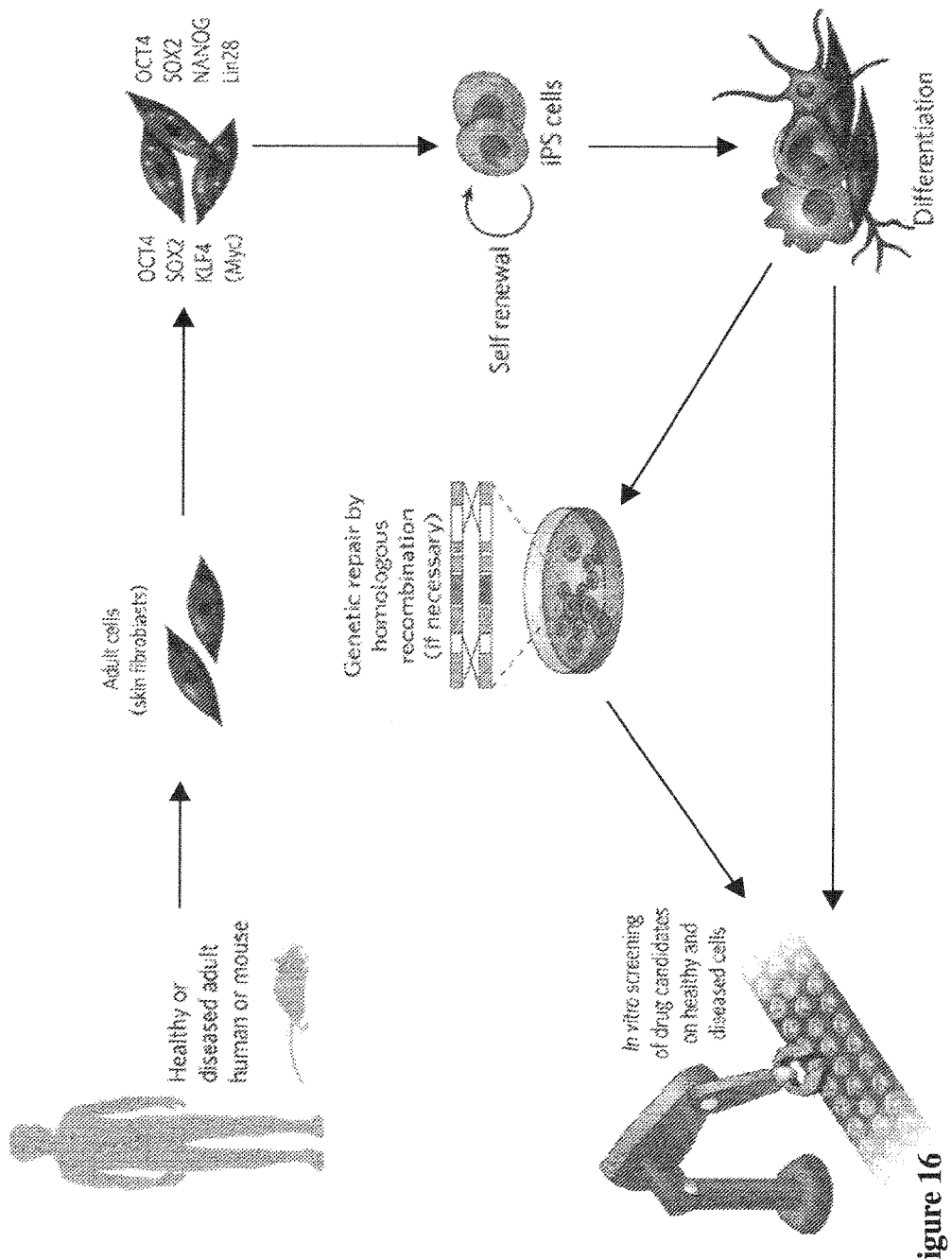
FIG. 16 shows the piPS cells can be used for drug screen and drug toxicity test as illustrated in this figure. For those patients who have genetic diseases, an extra step may have to take which include genetic repair by homologous recombination.
Figure 17:
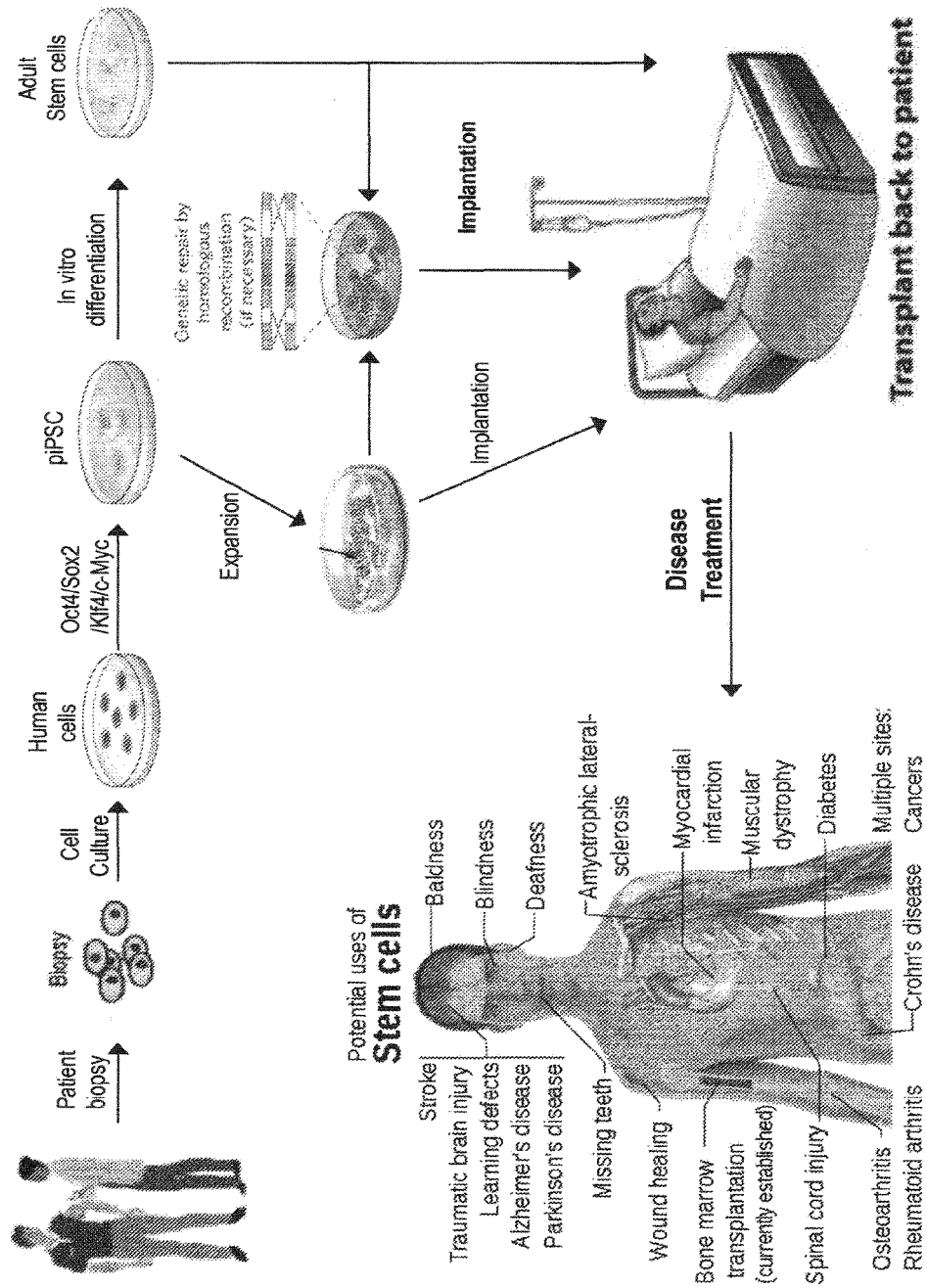
FIG. 17 shows the piPS cells can be used for patient-based stem cell therapy. Briefly, primary dermal fibroblasts can be obtained from a patient and these fibroblasts can be used to generate piPS cells by delivery of four reprogramming proteins. The generated piPS cells can be either expanded or led to specific lineage of adult stem cells. These piPS cells and adult stem cells can be transplanted into individual patients to treat specific disease. For those patients who have genetic diseases, an extra step may have to take which include genetic repair by homologous recombination before patient transplantation.

Major concerns have been raised about the quality of the generated iPSCs using the current iPSC methods. Results indicated slight pattern differences in epigenetic changes between the generated iPSCs and human ESCs. Rather than being reset to an embryo-like state, methylation patterns near the tips and centers of chromosomes in the iPSCs resembled those in the adult tissues from which the iPSCs had been derived. To solve this problem, an efficient cell reprogramming method has to be developed that completely resets the epigenetic clock of the starting somatic cells to return to an ESC-like state. In addition, most current iPSC/ piPSC methods use oncogenes that may increase the mutational rate. Data reported recently demonstrated that pre-existing and new mutations that occur during and after reprogramming contribute to the high mutational load found in the current hiPSC lines. Selection during cell reprogramming, colony picking and subsequent clonal expansion might be the contributing factors. Indeed, if the reprogramming efficiency is enhanced to a level such that no colony picking and clonal expansion are necessary, the resulting hiPSCs could be potentially free of mutations. The piPSC technique disclosed herein provides such high reprogramming efficiency. Furthermore, new reprogramming proteins, such as DNA de-methylases or methylcytosine dioxygenases, may be required to completely reset the epigenetic clock of the starting somatic cells, this piPSC technique disclosed herein can be used to screen these new reprogramming factors in a high-throughput fashion. Finally, since tedious colony selection during reprogramming and colony picking/cional expansion are avoided that may generate human piPSCs free of mutations, this offers a cell reprogramming technique that significantly enhances the quality of the generated piPSCs for future safe human clinical applications (FIGS. 15-17).

Throughout this application, author and year and patents by number reference various publications, including United States patents. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used herein, is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

TABLE 1

Numbers of colonies versus reprogramming protein concentrations using the same reprogramming procedure.

| No | Cycles | Condition | Ratio | No experiment | Starting cells | Protein concentration | Time | Number of colonies |
|---|---|---|---|---|---|---|---|---|
| 1 | 2 | 5 h/19 h | 1:1:1:0.1 | 3 | $10^5$ | 2 (μg/ml) | 5 days | 120 ± 20 |
| 2 | 2 | 5 h/19 h | 1:1:1:0.1 | 3 | $10^5$ | 1 (μg/ml) | 5 | 220 ± 30 |
| 3 | 2 | 5 h/19 h | 1:1:1:0.1 | 3 | $10^5$ | 0.50 (μg/ml) | 5 days | 505 ± 25 |
| 4 | 2 | 5 h/19 h | 1:1:1:0.1 | 3 | $10^5$ | 0.25 (μg/ml) | 5 days | 520 ± 13 |

We performed 2 cycles of protein reprogramming, each cycle contained a 5-hour incubation with four reprogramming proteins and a 19-hour incubation without proteins. The protein ratio is: Oct4:Sox2:Klf4:c-Myc = 1:1:1:0.1. We started with the same number of HNF cells and performed triplicte for each experimental condition. The colony numbers were counted at day 5 and reported as the mean and standard deviations (mean ± standard deviation). The generated piPS cell colonies were stained with AP (an early pluripotent marker) at day 5 and Rex-1 at day 8 (a late pluripotent marker).

TABLE 2

Percentage of the positively immunostained cells using different pluripotent markers at different time points during the time course that is shown in FIG. 4.

| | ALP | Nanog | Oct4 | Rex1 | Tra1-60 |
|---|---|---|---|---|---|
| 24-hour | 73% (438) | 74% (530) | 80% (547) | 83% (517) | 72% (340) |
| 48-hour | 79% (387) | 74% (338) | 83% (309) | 84% (350) | 80% (289) |
| 72-hour | 79% (265) | 83% (334) | 78% (425) | 87% (280) | 84% (221) |
| 108 hour | 86% (308) | 87% (355) | 86% (378) | 90% (387) | 87% (277) |

The percentage shown here is the percentage of positively stained cells with five different pluripotency markers.

Percentage=positively stained cells/total cell counted.

The number in the bracket is the total number of cells counted for calculation of positively stained cells.

TABLE 3

A table of conversion efficiency of piPS cell generation from human newborn fibroblast using different combinations of Sox2, Oct4 and Nanog, showing conversion efficiency ranges 84-90%. The conversion efficiency of the SON factors is 90 ± 3.5%. The numbers in the bracket are the cell numbers counted for calculation of conversion efficiency.

| Markers | Nanog (N) | Oct4 (O) | Nanog/Oct4 (NO) | Sox2/Oct4 (SO) | Sox2/Oct4/Nanog (SON) |
|---|---|---|---|---|---|
| Nanog | 81 ± 1 (639) | 83 ± 3 (661) | 86 ± 4 (890) | 88 ± 2 (593) | 87 ± 5 (856) |
| Oct4 | 85 ± 5 (800) | 85 ± 5 (713) | 91 ± 1 (716) | 85 ± 4 (820) | 93 ± 3 (856) |
| Rex1 | 90 ± 2 (965) | 85 ± 4 (788) | 91 ± 1 (777) | 92 ± 2 (1207) | 94 ± 2 (613) |
| Tra1-60 | 85 ± 1 (271) | — | 84 ± 2 (738) | — | 86 ± 3 (290) |
| Average | 85.3 ± 4% | 84.3 ± 1% | 88 ± 3% | 88.3 ± 2.8% | 90 ± 3.5% |

A minimum of 10 randomly selected fields was scored for positively and negatively stained cells in a triple-blinded manner to minimize subjective interpretations (>300 cells). We calculated conversion efficiency using the ratio of positive cells/total cells.

REFERENCES

1. Vazin T, Freed W J. Human embryonic stem cells: derivation, culture, and differentiation: a review. Restor Neurol Neurosci. 2010; 28(4):589-603.
2. Bahadur G, Morrison M, Machin L. Beyond the 'embryo question': human embryonic stem cell ethics in the context of biomaterial donation in the UK. Reprod Biomed Online. 2010 December; 21 (7):868-74.
3. Hemmat S, Lieberman D M, Most S P. An introduction to stem cell biology. Facial Plast Surg. 2010 October; 26(5): 343-9.
4. http://en.wikipedia.org/wiki/Cell_potency
5. Lerou P H, Daley G Q. Therapeutic potential of embryonic stem cells. Blood Rev. 2005 November; 19(6):321-31.
6. http://www.eurostemcell.org/faq/what-are-potential-applications-stem-cell-rescarch
7. Amit M, Shariki C, Margulets V, Itskovitz-Eldor J. Feeder layer- and serum-free culture of human embryonic stem cells. Biol Reprod. 2004 March; 70(3):837-45.
8. Ilic D. Culture of human embryonic stem cells and the extracellular matrix microenvironment Regen Med. 2006 January; 1 (1):95-101.
9. Takahashi K, Yamanaka S. (2006). Induction of pluripotent stem cells from mouse embryonic and adult fibroblast cultures by defined factors. Cell. 126:663-76.
10. Amabile G, Meissner A. (2009). Induced pluripotent stem cells: current progress and potential for regenerative medicine. Trends Mol Med. 15:59-68.
11. Lister R, Pelizzola M, Kida Y S, Hawkins R D, Nery J R, Hon G, Antosiewicz-Bourget J, O'Malley R, Castanon R, Klugman S, Downes M, Yu R, Stewart R, Ren B, Thomson J A, Evans R M, Ecker J R. (2011). Hotspots of aberrant epigenomic reprogramming in human induced pluripotent stem cells. Nature. 471, 68-73.
12. Lee H, Park J, Forget B G, Gaines P. (2009). Induced pluripotent stem cells in regenerative medicine: an argument for continued research on human embryonic stem cells. Regen Med. 4:759-69.
13. Kiskinis E, Eggan K. (2010). Progress toward the clinical application of patient-specific pluripotent stem cells. J Clin Invest. 120:51-9.
14. Okita K, lchisaka T, Yamanaka S. (2007). Generation of germ line-competent induced pluripotent stem cells. Nature. 448:313-7.
15. Maherali, N., Sridharan, R., Xie, W., Utikal, J., Eminli, S., Arnold, K, Stadtfeld, M., Yachechko, Y., Tchieu, J., Jaenisch, R., et al. (2007). Global epigenetic remodeling in directly reprogrammed fibroblasts. Cell Stem Cell 1, 55-70.
16. Wernig, M., Meissner, A., Foreman, R., Brambrink, T., Ku, M., Hochedlinger, K., Bernstein, B. E., and Jaenisch, R. (2007). In vitro reprogramming of fibroblasts into a pluripotent ES-cell-like state. Nature 448, 318-324.
17. Nakagawa, M., Koyanagi, M., Tanabe, K., Takahashi, K., Ischisaka, T., Aoi, T., Okita, K., Mochiduki, Y., Takizawa, N., and Yamanaka, S. (2008). Generation of induced pluripotent stem cells without Myc from mouse and human fibroblasts. Nat. Biotechnol. 26, 101-106.
18. Takahashi, K., Tanabe, K., Ohnuki, M., et al. (2007). Induction of pluripotent stem cells from adult human fibroblasts by defined factors. Cell, 131, 861-872.
19. Yu, J., Vodyanik, M. A., Smuga-Otto, K., et al. (2007). Induced pluripotent stem cell lines derived from human somatic cells. Science, 318, 1917-1920.
20. Park, I. H., Zhao, R., West, J. A., et al. (2008). Reprogramming of human somatic cells to pluripotency with defined factors. Nature, 451, 141-146.
21. Stadtfeld, M., Nagaya, M., Utikal, J., Weir, G., & Hochedlinger, K. (2008). Induced pluripotent stem cells generated without viral integration. Science, 322, 945-949.
22. Okita, K., Nakagawa, M., Hyenjong, H., Ichisaka, T., & Yamanaka, S. (2008). Generation of mouse induced pluripotent stem cells without viral vectors. Science, 322, 949-953.
23. Kaji K, Norrby K, Paca A, Mileikovsky M, Mohseni P, Woltjen K. Virus-free induction of pluripotency and subsequent excision of reprogramming factors. Nature 458, 771-775.
24. Woltjen, K., Michael, I. P., Mohseni, P., Desai, R., Mileikovsky, M., Hamalainen, R, Cowling, R., Wang, W., Liu, P., Gertsenstein, M., et al. (2009). piggyBac transposition reprograms fibroblasts to induced pluripotent stem cells. Nature 458, 766-770.
25. Soldner, F., Hockemeyer, D., Beard, C, Gao, Q., Bell, G. W., Cook, E. G., Hargus, G., Blak, A., Cooper, O., Mitalipova, M., et al. (2009). Parkinson's disease patient-derived induced pluripotent stem cells free of viral reprogramming factors. Cell 136, 964-977
26. Yu, J., Hu, K., Smuga-Otto, K., Tian, S., Stewart, R., Slukvin, and Thomson, J. A. (2009). Human induced pluripotent stem cells free of vector and transgene sequences Science 324, 797-801.
27. Zhou H, Wu S, Joo J Y, Zhu S, Han D W, Lin T, Trauger S, Bien G, Yao S, Zhu Y, Siuzdak G, Scholer H R, Duan L, Ding S. (2009). Generation of induced pluripotent stem cells using recombinant proteins. Cell Stem Cell. 4(5): 381-4.
28. Kim D, Kim C H, Moon J1, Chung Y G, Chang M Y, Han B S, Ko S, Yang E, Cha K Y, Lanza R, Kim K S. (2009). Generation of human induced pluripotent stem cells by direct delivery of reprogramming proteins. Cell Stem Cell. 4(6):472-6.
29. Warren, et al (2011) Highly Efficient Reprogramming to Pluripotency and Directed Differentiation of Human Cells with Synthetic Modified mRNA. Cell Stem Cell 7, 1-13.
30. Jalving M, Schepers H. (2009). Induced pluripotent stem cells: will they be safe? Curr Opin Mol Ther. 1:383-93.
31. Robbins R D, Prasain N, Maier B F, Yoder M C, Mirmira R G. (2010). Inducible pluripotent stem cells: not quite ready for prime time? Curr Opin Organ Transplant 15:61-7.
32. Rolletschek A, Wobus A M. (2009). Induced human pluripotent stem cells: promises and open questions. Biol Chem. 390:845-9.
33. Lister R, Pelizzola M, Kida Y S, Hawkins R D, Nery J R, Hon G, Antosiewicz-Bourget J, O'Mailey R, Castanon R, Klugman S, Downes M, Yu R, Stewart R, Ren B, Thomson J A, Evans R M, Ecker J R. (2011). Hotspots of aberrant epigenomic reprogramming in human induced pluripotent stem cells. Nature. 471, 68-73.
34. Kim K, Doi A, Wen B, Ng K, Zhao R, Cahan P, Kim J, Aryee M J, Ji H, Ehrlich L I, Yabuuchi A, Takeuchi A, Cunniff K C, Hongguang H, McKinney-Freeman S, Naveiras O, Yoon T J, Irizarry R A, Jung N, Seita J, Hanna J, Murakami P, Jaenisch R, Weissleder R, Orkin S H, Weissman I L, Feinberg A P, Daley G Q. (2010). Epigenetic memory in induced pluripotent stem cells. Nature. 467, 285-90.

35. Polo J M, Liu S, Figueroa M E, Kuialert W, Eminli S, Tan K Y, Apostolou E, Stadtfeld M, Li Y, Shioda T, Natesan S, Wagers A J, Melnick A, Evans T, Hochedlinger K. (2010). Cell type of origin influences the molecular and functional properties of mouse induced pluripotent stem cells. Nat Biotechnol. 28, 848-55.

36. Gore A, Li Z, Fung H L, Young J E, Agarwal S, Antosiewicz-Bourget J, Canto I, Giorgetti A, Israel M A, Kiskinis E, Lee J H, Loh Y H, Manos P D, Montserrat N, Panopoulos A D, Ruiz S, Wilbert M L, Yu J, Kirkness E F, Izpisua Belmonte J C, Rossi D J, Thomson J A, Eggan K, Daley G Q, Goldstein L S, Zhang K. (2011), Somatic coding mutations in human induced pluripotent stem cells. Nature, 471, 63-7.

37. Scheper W, Copray S. (2009). The molecular mechanism of induced pluripotency: two-stage switch. Stem Cell Rev. 5:204-23.

38. Carey B W, Markoulaki S, Hanna J, Saha K, Gao Q, Mitalipova M, Jaenisch R. Reprogramming of murine and human somatic cells using a single polycistronic vector. Proc Natl Acad Sci USA. 2009 Jan. 6; 106(1):157-62.

39. Shao L, Feng W, Sun Y, Bai H, Liu J, Currie C, Kim J, Gama R, Wang Z, Qian Z, Liaw L, Wu W S. Generation of iPS cells using defined factors linked via the self-cleaving 2A sequences in a single open reading frame. Cell Res. 2009 March; 19(3):296-306.

40. Ohnuki M, Takahashi K, Yamanaka S. Generation and characterization of human induced pluripotent stem cells. Curr Protoc Stem Cell Biol. 2009 June; Chapter 4:Unit 4A.2.

41. Trehin R, Merkle H P. (2004). Chances and pitfalls of cell penetrating peptides for cellular drug delivery. Eur J Pharm Biopharrn. 58:209-23.

42. Kabouridis P S. (2003) Biological applications of protein transduction technology. Trends Biotechnol. 21-0.498-503.

43. Sivashanmugam A, Meiners V, Cui C, Yang Y, Wang J & Li Q (2009). Practical protocols for production of very high-yield of recombinant proteins in *Eschericia coli*. Protein Science. 18:936-948.

44. Chan, E. M., et al., (2009). Live cell imaging distinguishes bona fide human iPS cells from partially reprogrammed cells. Nat Biotechnol, 27(11): 1033-7.

45. Li, Q., Huang Y., Murray, V. Chen, J and Wang, J. (2011) A QQ-reagent based protein transduction technology with intracellular targeting capability. Nature, Biotechnology (Under Review).

46. Li, Q., Huang Y., Xiao N., Murray V, Chen J and J Wang (2008). Real Time Investigation of Protein Folding, Structure, and Dynamics in Living Cells. A invited review in Method in Cell Biology, Elsevier Inc. Editor: Bhanu Jena, 90, 287-325.

47. Li, Q. and Wang, J. (2008). The QQ series of protein transduction reagents and their applications. US patent (Submitted on May 28, 2008, Pending) (application Ser. No. 12/128,320).

48. Niwa H, Miyazaki J, Smith A G. (2000). Quantitative expression of Oct-3/4 defines differentiation, dedifferentiation or self-renewal of ES cells. Nat Genet. 24(4): 372-6. 49. Knoepfler P S. (2009). Deconstructing stem cell tumorigenicity: a roadmap to safe regenerative medicine. Stem Cells. 27(5):1050-6.

50. Cho H J, Lee C S, Kwon Y W, Paek J S, Lee S H, Hur J, Lee E J, Roh T Y, Chu I S, Leem S H, Kim Y, Kang H J, Park Y B, Kim H S. (2010). Induction of pluripotent stem cells from adult somatic cells by protein-based reprogramming without genetic manipulation. Blood. 16, 386-95

51. Rodin S, Domogatskaya A, Strom S, Hansson E M, Chien K R, Inzunza J, Hovatta O, Tryggvason K. (2010). Long-term self-renewal of human pluripotent stem cells on human recombinant laminin-511. Nat Biotechnol. 28, 611-5.

52. Raff M C, Abney E R, Cohen J, Lindsay R, Noble M. (1983). Two types of astrocytes in cultures of developing rat white matter: differences in morphology, surface gangliosides, and growth characteristics. J Neurosci. 3:1289-1300.

53. Jaenisch R, Young R. (2008). Stem cells, the molecular circuitry of pluripotency and nuclear reprogramming. Cell. 32, 567-82.

54. Hanna J, Saha K, Pando B, van Zon J, Lengner C J, Creyghton M P, van Oudenaarden A, Jaenisch R. (2009). Direct cell reprogramming is a stochastic process amenable to acceleration. Nature. 462:595-601.

55. Yu J, Vodyanik M A, Smuga-Otto K, Antossewicz-Bourget J, Frane J L, Tian S, Nte J, Jonsdoitir G A, Ruotti V, Stewart R, Slukvin I I, Thomson J A. (2007). Induced pluripotent stem cell lines derived from human somatic cells. Science. 318(5858): 1917-20.

56. Feng B, Jiang J, Kraus P, Ng J H, Heng J C, Chan Y S, Yaw L P, Zhang W, Loh Y H, Han J, Vega V B, Cacheux-Rataboul V, Lim B, Lufkin T, Ng H H. (2009). Reprogramming of fibroblasts into induced pluripotent stem cells with orphan nuclear receptor Esrrb. War Cell Biol. 11 (2): 197-203.

57. Lin S L, Chang D C, Chang-Lin S, Lin C H, Wu D T, Chen D T, Ying S Y. (2008). Mir-302 reprograms human skin cancer cells into a pluripotent ES-cell-like state. RNA. 14:2115-24.

58. Kim J B, Zaehres H, Wu G, Gentile L, Ko K, Sebastiano V, Arauzo-Bravo M J, Ruau D, Han D W, Zenke M, Scholer H R. (2008). Pluripotent stem cells induced from adult neural stem cells by reprogramming with two factors. Nature. 454:646-50.

59. Heng H H, Squire J, Tsui L C. (1992). High-resolution mapping of mammalian genes by in situ hybridization to free chromatin. Proc Natl Acad Sci USA. 89, 9509-3.

60. Heng H H, Stevens J B, Liu G, Bremer S W, Ye K J, Reddy P V, Wu G S, Wang Y A, Tainsky M A, Ye C J. (2006). Stochastic cancer progression driven by nonclonal chromosome aberrations. J Cell Physiol. 208, 461-72.

The invention claimed is:

1. A method of generating human protein-induced pluripotent stem cells (piPSC), comprising:
    i) producing reprogramming proteins by bacterial expression, wherein the reprogramming proteins comprise the combination of Sox2, Oct4 and Nanog;
    ii) modifying the bacterially expressed reprogramming proteins produced from step i) by mixing the proteins with a QQ-reagent comprising polyethylenimine (PEI) and DOTAP/DOPE;
    iii) delivering the modified reprogramming proteins produced from step ii) into nuclei of starting human somatic cells or human diseased somatic cells, using a QQ-protein transduction technique;
    iv) repeating several cell reprogramming cycles sufficient to create human reprogrammed piPSC;

v) moving human reprogrammed piPSC from step iv into a feeder-free medium for expansion; and vi) expanding and passaging the human reprogrammed piPSC from step v) as a whole dish of cells, with the proviso that colony picking is not performed, thereby generating homogeneous human piPSC.

2. The method according to claim 1, further including the step of in vitro labeling the reprogramming proteins with a small molecule fluorescence probe prior to said modifying step (ii).

3. The method according to claim 2, further including monitoring the efficiency of QQ-protein delivery into the nuclei of the starting human somatic cells or human diseased somatic cells.

4. The method according to claim 1, further comprising differentiating the piPSC into a cell type selected from the group consisting of: specific adult stem cells, specific progenitor cells and a different somatic cell type compared to the starting human somatic cells or human diseased somatic cells.

* * * * *